United States Patent
Huang et al.

(10) Patent No.: US 11,680,046 B2
(45) Date of Patent: Jun. 20, 2023

(54) CRYSTALLINE (R)-5-CARBAMOYLPYRIDIN-3-YL-2-METHYL-4-(3-(TRIFLUOROMETHOXY)BENZYL)PIPERAZINE-1-CARBOXYLATE, COMPOSITIONS AND METHODS OF USE THEREOF

(71) Applicants: Celgene Corporation, Summit, NJ (US); Lundbeck La Jolla Research Center, Inc., San Diego, CA (US)

(72) Inventors: Lianfeng Huang, Basking Ridge, NJ (US); Nancy Tsou, Edison, NJ (US); Nicole Suzanne White, San Diego, CA (US); Jun Xu, Suzhou (CN); Qun Zhang, Suzhou (CN)

(73) Assignees: Celgene Corporation, Summit, NJ (US); Lundbeck La Jolla Research Center, Inc., San Diego, CA (US)

( * ) Notice: Subject to any disclaimer, the term of this patent is extended or adjusted under 35 U.S.C. 154(b) by 189 days.

(21) Appl. No.: 17/338,182

(22) Filed: Jun. 3, 2021

(65) Prior Publication Data

US 2021/0363105 A1 Nov. 25, 2021

Related U.S. Application Data

(62) Division of application No. 16/569,578, filed on Sep. 12, 2019, now Pat. No. 11,053,199.

(60) Provisional application No. 62/731,014, filed on Sep. 13, 2018.

(51) Int. Cl.
   *C07D 211/94* (2006.01)
   *A61P 35/00* (2006.01)

(52) U.S. Cl.
   CPC ............ *C07D 211/94* (2013.01); *A61P 35/00* (2018.01); *C07B 2200/13* (2013.01)

(58) Field of Classification Search
   CPC .... C07D 211/94; C07B 2200/13; A61P 35/00
   See application file for complete search history.

(56) References Cited

U.S. PATENT DOCUMENTS

| | | |
|---|---|---|
| 2010/0009971 A1 | 1/2010 | Ishii et al. |
| 2018/0256566 A1 | 9/2018 | Grice et al. |
| 2019/0282568 A1 | 9/2019 | Grice et al. |

FOREIGN PATENT DOCUMENTS

| | | | | |
|---|---|---|---|---|
| WO | WO 2018/169880 | * | 9/2018 | ........... A61K 31/497 |
| WO | WO 2018169880 A1 | | 9/2018 | |

OTHER PUBLICATIONS

Bernstein, 2004, "Crystal Structure Prediction and Polymorphism," *ACA Transactions*, 39:14-23.
Braga et al., 2005, "Making crystals from crystals: a green route to crystal engineering and polymorphism," *Chemical Communications*, 3635-3645.
Chemburkar et al., 2000, "Dealing with the Impact of Ritonavir Polymorphs on the Late Stages of Bulk Drug Process Development," *Organic Process Research & Development*, 4(5):413-417.
Di Martino et al., 1997, "Preparation and Physical Characterization of Forms II and III of Paracetamol," *Journal of Thermal Analysis*, 48(3):447-458.
Jones et al., 2011, "Pharmaceutical Cocrystals: An Emerging Approach to Physical Property Enhancement," *MRS Bulletin*, 31:875-879.
Knapman et al., 2000, "Polymorphic predictions," *Modern Drug Discovery*, 3:53-57.
Price, 2004, "The computational prediction of pharmaceutical crystal structures and polymorphism," *Advanced Drug Delivery Reviews*, 56(3):301-319.

* cited by examiner

*Primary Examiner* — Erich A Leeser
(74) *Attorney, Agent, or Firm* — Jones Day

(57) ABSTRACT

Provided herein are crystalline forms of (R)-5-carbamoylpyridin-3-yl-2-methyl-4-(3-(trifluoromethoxy)benzyl)piperazine-1-carboxylate. Pharmaceutical compositions comprising crystalline forms of (R)-5-carbamoylpyridin-3-yl-2-methyl-4-(3-(trifluoromethoxy)benzyl)piperazine-1-carboxylate are also disclosed.

12 Claims, 14 Drawing Sheets

CRYSTALLINE (R)-5-CARBAMOYLPYRIDIN-3-YL-2-METHYL-4-(3-(TRIFLUOROMETHOXY)BENZYL)PIPERAZINE-1-CARBOXYLATE, COMPOSITIONS AND METHODS OF USE THEREOF

CROSS-REFERENCE

This application is a divisional application of U.S. application Ser. No. 16/569,578, filed Sep. 12, 2019, which claims the benefit of U.S. Provisional Application No. 62/731,014, filed on Sep. 13, 2018, the disclosure of each of which is herein incorporated by reference in its entirety.

FIELD

Provided herein are solid forms of (R)-5-carbamoylpyridin-3-yl-2-methyl-4-(3-(trifluoromethoxy)benzyl)piperazine-1-carboxylate. Pharmaceutical compositions comprising such solid forms and methods of use for treating, preventing, and managing various disorders are also provided herein.

BACKGROUND

Many compounds can exist in different crystal forms, or polymorphs, which exhibit different physical, chemical, and spectroscopic properties. For example, certain polymorphs of a compound may be more readily soluble in particular solvents, may flow more readily, or may compress more easily than others. See, e.g., P. DiMartino, et al., *J. Thermal Anal.,* 48:447-458 (1997). In the case of drugs, certain solid forms may be more bioavailable than others, while others may be more stable under certain manufacturing, storage, and biological conditions.

Polymorphic forms of a compound are known in the pharmaceutical arts to affect, for example, the solubility, stability, flowability, fractability, and compressibility of the compound, as well as the safety and efficacy of drug products comprising it. See, e.g., Knapman, K. *Modern Drug Discoveries,* 2000, 53. Therefore, the discovery of new polymorphs of a drug can provide a variety of advantages.

The identification and selection of a solid form of a pharmaceutical compound are complex, given that a change in solid form may affect a variety of physical and chemical properties, which may provide benefits or drawbacks in processing, formulation, stability, bioavailability, storage, handling (e.g., shipping), among other important pharmaceutical characteristics. Useful pharmaceutical solids include crystalline solids and amorphous solids, depending on the product and its mode of administration. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability.

The importance of discovering polymorphs was underscored by the case of Ritonavir™, an HIV protease inhibitor that was formulated as soft gelatin capsules. About two years after the product was launched, the unanticipated precipitation of a new, less soluble polymorph in the formulation necessitated the withdrawal of the product from the market until a more consistent formulation could be developed (see S. R. Chemburkar et al., *Org. Process Res. Dev.,* (2000) 4:413-417).

Notably, it is not possible to predict apriori if crystalline forms of a compound even exist, let alone how to successfully prepare them (see, e.g., Braga and Grepioni, 2005, "Making crystals from crystals: a green route to crystal engineering and polymorphism," *Chem. Commun.*:3635-3645 (with respect to crystal engineering, if instructions are not very precise and/or if other external factors affect the process, the result can be unpredictable); Jones et al., 2006, Pharmaceutical Cocrystals: An Emerging Approach to Physical Property Enhancement," *MRS Bulletin* 31:875-879 (At present it is not generally possible to computationally predict the number of observable polymorphs of even the simplest molecules); Price, 2004, "The computational prediction of pharmaceutical crystal structures and polymorphism," *Advanced Drug Delivery Reviews* 56:301-319 ("Price"); and Bernstein, 2004, "Crystal Structure Prediction and Polymorphism," *ACA Transactions* 39:14-23 (a great deal still needs to be learned and done before one can state with any degree of confidence the ability to predict a crystal structure, much less polymorphic forms)).

The variety of possible solid forms creates potential diversity in physical and chemical properties for a given pharmaceutical compound. The discovery and selection of solid forms are of great importance in the development of an effective, stable and marketable pharmaceutical product.

(R)-5-Carbamoylpyridin-3-yl-2-methyl-4-(3-(trifluoromethoxy)benzyl)piperazine-1-carboxylate is a compound which is a dual MAGL and FAAH inhibitor, and may be used in treating various disorders.

The synthesis of (R)-5-carbamoylpyridin-3-yl-2-methyl-4-(3-(trifluoromethoxy)benzyl)piperazine-1-carboxylate has been described in PCT/US2018/022049 filed Mar. 12, 2018.

Novel crystalline forms of (R)-5-carbamoylpyridin-3-yl-2-methyl-4-(3-(trifluoromethoxy)benzyl)piperazine-1-carboxylate are described herein. New polymorphic forms of (R)-5-carbamoylpyridin-3-yl-2-methyl-4-(3-(trifluoromethoxy)benzyl)piperazine-1-carboxylate can further the development of formulations for the treatment of various illnesses, and may yield numerous formulation, manufacturing and therapeutic benefits.

SUMMARY

Provided herein are crystalline forms of (R)-5-carbamoylpyridin-3-yl-2-methyl-4-(3-(trifluoromethoxy)benzyl)piperazine-1-carboxylate. Also provided herein are pharmaceutical compositions comprising crystalline forms of (R)-5-carbamoylpyridin-3-yl-2-methyl-4-(3-(trifluoromethoxy)benzyl)piperazine-1-carboxylate. Further provided herein are methods of treating or preventing a variety of disease and disorders, which comprise administering to a patient a therapeutically effective amount of a crystalline form of (R)-5-carbamoylpyridin-3-yl-2-methyl-4-(3-(trifluoromethoxy)benzyl)piperazine-1-carboxylate.

Also provided herein are methods of preparing, isolating, and characterizing crystalline (R)-5-carbamoylpyridin-3-yl-2-methyl-4-(3-(trifluoromethoxy)benzyl)piperazine-1-carboxylate.

DEFINITIONS

Figure 1:
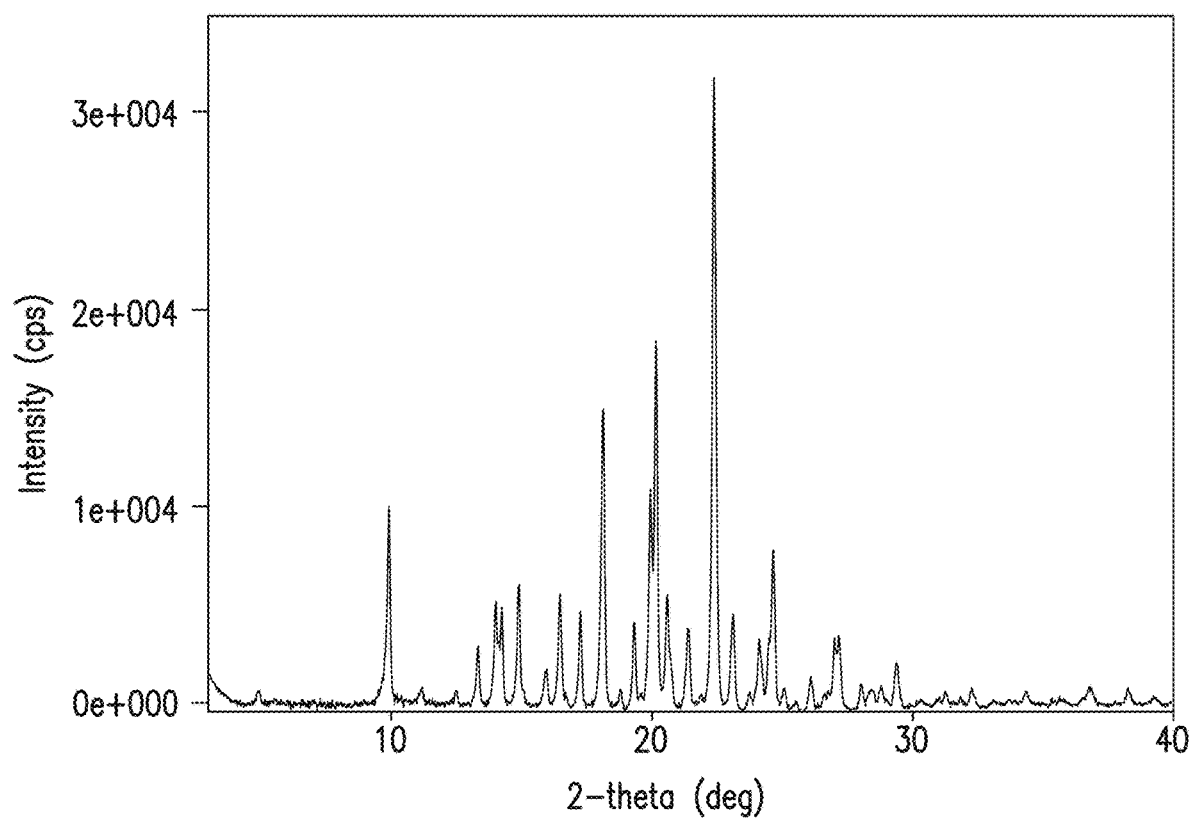
FIG. 1 provides a representative X-ray powder diffraction (XRPD) pattern of crystalline (R)-5-carbamoylpyridin-3-yl-2-methyl-4-(3-(trifluoromethoxy)benzyl)piperazine-1-carboxylate Form A.

As used herein, and unless otherwise specified, the compound referred to herein as (R)-5-carbamoylpyridin-3-yl-2-methyl-4-(3-(trifluoromethoxy)benzyl)piperazine-1-carboxylate corresponds to a compound of Formula (I), depicted below.

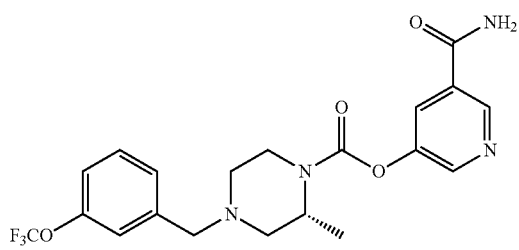

(R)-5-Carbamoylpyridin-3-yl-2-methyl-4-(3-(trifluoromethoxy)benzyl)piperazine-1-carboxylate can be obtained via standard, synthetic methods (see e.g., PCT/US2018/022049).

Unless otherwise specified, the term "crystalline" and related terms used herein, when used to describe a substance, component, product, or form, mean that the substance, component, product, or form is substantially crystalline, for example, as determined by X-ray diffraction. (see, e.g., Remington's Pharmaceutical Sciences, 20$^{th}$ ed., Lippincott Williams & Wilkins, Philadelphia Pa., 173 (2000); The United States Pharmacopeia, 37$^{th}$ ed., 503-509 (2014)).

As used herein, and unless otherwise specified, the terms "about" and "approximately," when used in connection with doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. In certain embodiments, the terms "about" and "approximately," when used in this context, contemplate a dose, amount, or weight percent within 30%, within 20%, within 15%, within 10%, or within 5%, of the specified dose, amount, or weight percent.

As used herein, and unless otherwise specified, the terms "about" and "approximately," when used in connection with a numeric value or range of values which is provided to characterize a particular solid form, e.g., a specific temperature or temperature range, such as, for example, that describes a melting, dehydration, desolvation, or glass transition temperature; a mass change, such as, for example, a mass change as a function of temperature or humidity; a solvent or water content, in terms of, for example, mass or a percentage; or a peak position, such as, for example, in analysis by, for example, IR or Raman spectroscopy or XRPD; indicate that the value or range of values may deviate to an extent deemed reasonable to one of ordinary skill in the art while still describing the solid form. Techniques for characterizing crystal forms and amorphous forms include, but are not limited to, thermal gravimetric analysis (TGA), differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility studies, and dissolution studies. In certain embodiments, the terms "about" and "approximately," when used in this context, indicate that the numeric value or range of values may vary within 30%, 20%, 15%, 10%, 9%, 8%, 7%, 6%, 5%, 4%, 3%, 2%, 1.5%, 1%, 0.5%, or 0.25% of the recited value or range of values. In the context of molar ratios, "about" and "approximately" indicate that the numeric value or range of values may vary within 20%, 15%, 10%, 9%, 8%, 7%, 6%, 5%, 4%, 3%, 2%, 1.5%, 1%, 0.5%, or 0.25% of the recited value or range of values. It should be understood that the numerical values of the peaks of an X-ray powder diffraction pattern may vary from one machine to another, or from one sample to another, and so the values quoted are not to be construed as absolute, but with an allowable variability, such as ±0.2 degrees two theta (°2θ), or more. For example, in some embodiments, the value of an XRPD peak position may vary by up to ±0.2 degrees 2θ while still describing the particular XRPD peak.

As used herein, and unless otherwise specified, a solid form that is "substantially physically pure" is substantially free from other solid forms. In certain embodiments, a crystal form that is substantially physically pure contains less than about 50%, 45%, 40%, 35%, 30%, 25%, 20%, 15%, 10%, 9%, 8%, 7%, 6%, 5%, 4%, 3%, 2%, 1%, 0.5%, 0.4%, 0.3%, 0.2%, 0.1%, 0.05%, or 0.01% of one or more other solid forms on a weight basis. The detection of other solid forms can be accomplished by any method apparent to a person of ordinary skill in the art, including, but not limited to, diffraction analysis, thermal analysis, elemental combustion analysis and/or spectroscopic analysis.

As used herein, and unless otherwise specified, a solid form that is "substantially chemically pure" is substantially free from other chemical compounds (i.e., chemical impurities). In certain embodiments, a solid form that is substantially chemically pure contains less than about 50%, 45%, 40%, 35%, 30%, 25%, 20%, 15%, 10%, 9%, 8%, 7%, 6%, 5%, 4%, 3%, 2%, 1%, 0.5%, 0.4%, 0.3%, 0.2%, 0.10%, 0.05%, or 0.01% of one or more other chemical compounds on a weight basis. The detection of other chemical compounds can be accomplished by any method apparent to a person of ordinary skill in the art, including, but not limited to, methods of chemical analysis, such as, e.g., mass spectrometry analysis, spectroscopic analysis, thermal analysis, elemental combustion analysis and/or chromatographic analysis.

As used herein, and unless otherwise indicated, a chemical compound, solid form, or composition that is "substantially free" of another chemical compound, solid form, or composition means that the compound, solid form, or composition contains, in certain embodiments, less than about 50%, 45%, 40%, 35%, 30%, 25%, 20%, 15%, 10%, 9%, 8%, 7%, 6%, 5%, 4%, 3%, 2%, 1%, 0.5%, 0.4%, 0.3%, 0.2% 0.1%, 0.05%, or 0.01% by weight of the other compound, solid form, or composition.

Unless otherwise specified, the terms "anhydrate" and "anhydrous" as used herein, refer to a solid form of a substance which does not contain water in its crystal lattice.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound provided herein, with or without other additional active agents, after the onset of symptoms of a particular disease.

Unless otherwise specified, the term "composition" as used herein is intended to encompass a product comprising the specified ingredient(s) (and in the specified amount(s), if indicated), as well as any product which results, directly or indirectly, from combination of the specified ingredient(s) in the specified amount(s). By "pharmaceutically acceptable," it is meant a diluent, excipient, or carrier in a formulation must be compatible with the other ingredient(s) of the formulation and not deleterious to the recipient thereof.

Unless otherwise specified, the term "subject" is defined herein to include animals, such as mammals, including, but not limited to, primates (e.g., humans), cows, sheep, goats, horses, dogs, cats, rabbits, rats, mice, and the like. In specific embodiments, the subject is a human.

Unless otherwise specified, to the extent that there is a discrepancy between a depicted chemical structure of a compound provided herein and a chemical name of a compound provided herein, the chemical structure shall control.

DETAILED DESCRIPTION

Provided herein are solid forms of (R)-5-carbamoylpyridin-3-yl-2-methyl-4-(3-(trifluoromethoxy)benzyl)piperazine-1-carboxylate. In certain embodiments, the solid form is crystalline. In certain embodiments, the solid form is a single-component solid form. In certain embodiments, the solid form is an anhydrate.

Crystalline forms of (R)-5-carbamoylpyridin-3-yl-2-methyl-4-(3-(trifluoromethoxy)benzyl)piperazine-1-carboxylate can be prepared by the methods described herein, including the methods described in the Examples below, or by techniques known in the art, including heating, cooling, freeze drying, lyophilization, solvent evaporation, solvent recrystallization, antisolvent addition, slurry recrystallization, rapid cooling, slow cooling, exposure to solvent and/or water, and drying. The particle size of the resulting solid forms, which can vary, e.g., from nanometer dimensions to millimeter dimensions, can be controlled, e.g., by varying crystallization conditions, such as, e.g., the rate of crystallization and/or the crystallization solvent system, or by particle-size reduction techniques, e.g., grinding, milling, micronizing or sonication.

While not intending to be bound by any particular theory, crystalline forms of (R)-5-carbamoylpyridin-3-yl-2-methyl-4-(3-(trifluoromethoxy)benzyl)piperazine-1-carboxylate are characterized by physical properties, e.g., stability, solubility and dissolution rate, appropriate for pharmaceutical and therapeutic dosage forms. Moreover, while not wishing to be bound by any particular theory, crystalline forms of (R)-5-carbamoylpyridin-3-yl-2-methyl-4-(3-(trifluoromethoxy)benzyl)piperazine-1-carboxylate are characterized by physical properties (e.g., density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain crystalline forms suitable for the manufacture of a dosage form. Such properties can be determined using particular analytical chemical techniques, including solid-state analytical techniques (e.g., X-ray diffraction, microscopy, spectroscopy and thermal analysis), as described herein and known in the art.

Certain embodiments herein provide compositions comprising crystalline (R)-5-carbamoylpyridin-3-yl-2-methyl-4-(3-(trifluoromethoxy)benzyl)piperazine-1-carboxylate.

Certain embodiments provide methods of using these compositions in the treatment, prevention or management of diseases and disorders including, but not limited to, diseases and disorders related to MAGL and/or FAAH activity.

Certain embodiments herein provide methods of using crystalline forms of (R)-5-carbamoylpyridin-3-yl-2-methyl-4-(3-(trifluoromethoxy)benzyl)piperazine-1-carboxylate in the treatment, prevention, or management of pain, neurological disorders, anxiety, inflammatory bowel disease, neuropathic pain, and the proliferation and migration of cancer cells.

Certain embodiments herein provide crystalline (R)-5-carbamoylpyridin-3-yl-2-methyl-4-(3-(trifluoromethoxy)benzyl)piperazine-1-carboxylate Form A.

In one embodiment provided herein, crystalline (R)-5-carbamoylpyridin-3-yl-2-methyl-4-(3-(trifluoromethoxy)

benzyl)piperazine-1-carboxylate Form A can be obtained from methanol. In one embodiment provided herein, crystalline (R)-5-carbamoylpyridin-3-yl-2-methyl-4-(3-(trifluoromethoxy)benzyl)piperazine-1-carboxylate Form A can be obtained from isopropyl acetate. In one embodiment provided herein, crystalline (R)-5-carbamoylpyridin-3-yl-2-methyl-4-(3-(trifluoromethoxy)benzyl)piperazine-1-carboxylate Form A can be obtained from a 9:1 ethanol/water mixture. In one embodiment provided herein, crystalline (R)-5-carbamoylpyridin-3-yl-2-methyl-4-(3-(trifluoromethoxy)benzyl)piperazine-1-carboxylate Form A can be obtained from toluene.

In certain embodiments, crystalline (R)-5-carbamoylpyridin-3-yl-2-methyl-4-(3-(trifluoromethoxy)benzyl)piperazine-1-carboxylate Form A may be characterized by X-ray powder diffraction analysis.

In one embodiment, provided is crystalline (R)-5-carbamoylpyridin-3-yl-2-methyl-4-(3-(trifluoromethoxy)benzyl) piperazine-1-carboxylate Form A having an X-ray powder diffraction pattern comprising peaks at 16.5, 20.1, and 22.3 degrees 2θ±0.2 degrees 2θ.

In one embodiment, provided is crystalline (R)-5-carbamoylpyridin-3-yl-2-methyl-4-(3-(trifluoromethoxy)benzyl) piperazine-1-carboxylate Form A having an X-ray powder diffraction pattern comprising peaks at 16.4, 20.1, and 22.3 degrees 2θ+0.2 degrees 2θ.

In one embodiment, provided is crystalline (R)-5-carbamoylpyridin-3-yl-2-methyl-4-(3-(trifluoromethoxy)benzyl) piperazine-1-carboxylate Form A having an X-ray powder diffraction pattern comprising peaks at 18.1, 20.1, and 22.3 degrees 2θ±0.2 degrees 2θ.

In one embodiment, provided is crystalline (R)-5-carbamoylpyridin-3-yl-2-methyl-4-(3-(trifluoromethoxy)benzyl) piperazine-1-carboxylate Form A wherein the X-ray powder diffraction pattern further comprises peaks at 9.9, 19.9, and 24.6 degrees 2θ 0.2 degrees 2θ.

In one embodiment, provided is crystalline (R)-5-carbamoylpyridin-3-yl-2-methyl-4-(3-(trifluoromethoxy)benzyl) piperazine-1-carboxylate Form A wherein the X-ray powder diffraction pattern further comprises peaks at 9.9, 19.9, and 24.7 degrees 2θ+0.2 degrees 2θ.

In certain embodiments, crystalline (R)-5-carbamoylpyridin-3-yl-2-methyl-4-(3-(trifluoromethoxy)benzyl)piperazine-1-carboxylate Form A is characterized by XRPD peaks located at one, two, three, four, five, six, seven, eight, nine, ten, eleven, twelve, thirteen, or fourteen of the following approximate positions: 9.9, 13.3, 13.9, 14.8, 16.4, 18.0, 19.9, 20.1, 22.3, 23.0, 24.4, 24.6, 26.9, and 29.3 degrees 2θ. In certain embodiments, crystalline (R)-5-carbamoylpyridin-3-yl-2-methyl-4-(3-(trifluoromethoxy)benzyl)piperazine-1-carboxylate Form A is characterized by an XRPD pattern having 1, 2, 3, 4, 5, 6, 7, 8, 9, 10, 11, 12, 13, 14, 15, 16, 17, 18, 19, 20, 21, 22, 23, 24 or 25 peaks matching peaks in the representative XRPD pattern provided herein.

In certain embodiments, crystalline (R)-5-carbamoylpyridin-3-yl-2-methyl-4-(3-(trifluoromethoxy)benzyl)piperazine-1-carboxylate Form A is characterized by XRPD peaks located at one, two, three, four, five, six, seven, eight, nine, ten, eleven, twelve, thirteen, fourteen, fifteen, sixteen, seventeen, eighteen, nineteen, twenty, or twenty-one of the following approximate positions: 9.9, 13.4, 14.0, 14.2, 14.9, 16.0, 16.5, 17.3, 18.1, 19.3, 19.9, 20.1, 20.6, 21.4, 22.3, 23.1, 24.1, 24.7, 27.0, 27.2, and 29.3 degrees 2θ. In certain embodiments, crystalline (R)-5-carbamoylpyridin-3-yl-2-methyl-4-(3-(trifluoromethoxy)benzyl)piperazine-1-carboxylate Form A is characterized by an XRPD pattern having 1, 2, 3, 4, 5, 6, 7, 8, 9, 10, 11, 12, 13, 14, 15, 16, 17, 18, 19, 20, 21, 22, 23, 24 or 25 peaks matching peaks in the representative XRPD pattern provided herein.

In one embodiment, provided is crystalline (R)-5-carbamoylpyridin-3-yl-2-methyl-4-(3-(trifluoromethoxy)benzyl) piperazine-1-carboxylate Form A having an X-ray powder diffraction pattern corresponding to the representative X-ray powder diffraction pattern depicted in FIG. 1.

In certain embodiments, crystalline (R)-5-carbamoylpyridin-3-yl-2-methyl-4-(3-(trifluoromethoxy)benzyl)piperazine-1-carboxylate Form A may be characterized by thermal analysis.

In one embodiment, provided is crystalline (R)-5-carbamoylpyridin-3-yl-2-methyl-4-(3-(trifluoromethoxy)benzyl) piperazine-1-carboxylate Form A having a differential scanning calorimetry thermogram comprising an endotherm with a maximum at about 113° C.

In one embodiment, provided is crystalline (R)-5-carbamoylpyridin-3-yl-2-methyl-4-(3-(trifluoromethoxy)benzyl) piperazine-1-carboxylate Form A having a differential scanning calorimetry thermogram comprising an endotherm with a maximum at about 112° C.

In one embodiment, provided is crystalline (R)-5-carbamoylpyridin-3-yl-2-methyl-4-(3-(trifluoromethoxy)benzyl) piperazine-1-carboxylate Form A having a differential scanning calorimetry thermogram comprising an endotherm with an onset at about 112° C.

In one embodiment, provided is crystalline (R)-5-carbamoylpyridin-3-yl-2-methyl-4-(3-(trifluoromethoxy)benzyl) piperazine-1-carboxylate Form A having a differential scanning calorimetry thermogram comprising an endotherm with an onset at about 111° C.

Figure 2:
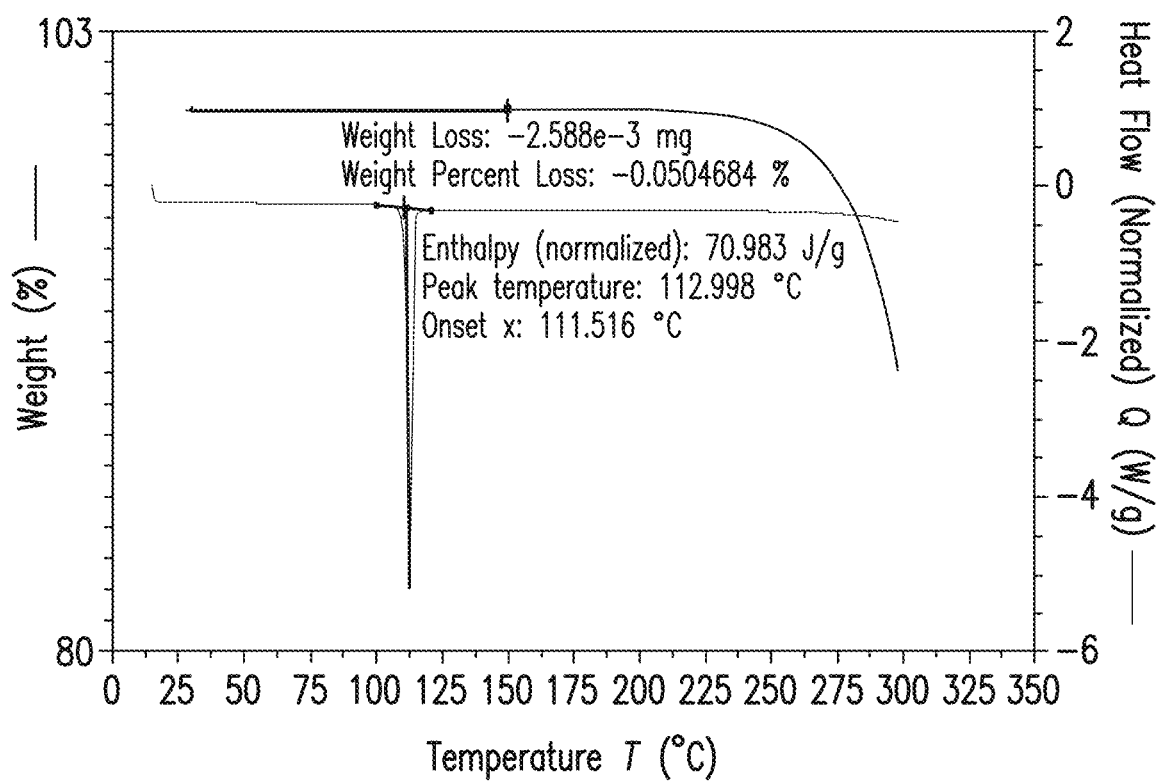
FIG. 2 provides a representative differential scanning calorimetry (DSC) thermogram and a representative thermogravimetric analysis (TGA) thermogram of crystalline (R)-5-carbamoylpyridin-3-yl-2-methyl-4-(3-(trifluoromethoxy)benzyl)piperazine-1-carboxylate Form A.

In one embodiment, provided is crystalline (R)-5-carbamoylpyridin-3-yl-2-methyl-4-(3-(trifluoromethoxy)benzyl) piperazine-1-carboxylate having a differential scanning calorimetry thermogram corresponding to the representative differential scanning calorimetry thermogram depicted in FIG. 2.

In one embodiment, provided is crystalline (R)-5-carbamoylpyridin-3-yl-2-methyl-4-(3-(trifluoromethoxy)benzyl) piperazine-1-carboxylate Form A which is anhydrous.

In one embodiment, provided is crystalline (R)-5-carbamoylpyridin-3-yl-2-methyl-4-(3-(trifluoromethoxy)benzyl) piperazine-1-carboxylate Form A having a thermogravimetric analysis thermogram comprising a weight loss of less than about 1.22% when heated from about 25° C. to about 100° C.

In one embodiment, provided is crystalline (R)-5-carbamoylpyridin-3-yl-2-methyl-4-(3-(trifluoromethoxy)benzyl) piperazine-1-carboxylate Form A having a thermogravimetric analysis thermogram comprising a weight loss of less than about 1.0% when heated from about 30° C. to about 150° C.

In one embodiment, provided is crystalline (R)-5-carbamoylpyridin-3-yl-2-methyl-4-(3-(trifluoromethoxy)benzyl) piperazine-1-carboxylate Form A having a thermogravimetric analysis thermogram comprising a weight loss of less than about 0.1% when heated from about 30° C. to about 150° C.

In one embodiment, provided is crystalline (R)-5-carbamoylpyridin-3-yl-2-methyl-4-(3-(trifluoromethoxy)benzyl) piperazine-1-carboxylate Form A having a thermogravimetric analysis thermogram corresponding to the representative thermogravimetric analysis thermogram depicted in FIG. 2.

In one embodiment, provided is crystalline (R)-5-carbamoylpyridin-3-yl-2-methyl-4-(3-(trifluoromethoxy)benzyl) piperazine-1-carboxylate Form A which is substantially physically pure.

In one embodiment, provided is crystalline (R)-5-carbamoylpyridin-3-yl-2-methyl-4-(3-(trifluoromethoxy)benzyl)piperazine-1-carboxylate Form A which is substantially chemically pure.

In one embodiment, provided is a pharmaceutical composition comprising crystalline (R)-5-carbamoylpyridin-3-yl-2-methyl-4-(3-(trifluoromethoxy)benzyl)piperazine-1-carboxylate Form A.

Certain embodiments herein provide crystalline (R)-5-carbamoylpyridin-3-yl-2-methyl-4-(3-(trifluoromethoxy)benzyl)piperazine-1-carboxylate Form B.

In one embodiment provided herein, crystalline (R)-5-carbamoylpyridin-3-yl-2-methyl-4-(3-(trifluoromethoxy)benzyl)piperazine-1-carboxylate Form B can be obtained from a 9:1 acetonitrile/water mixture. In one embodiment provided herein, crystalline (R)-5-carbamoylpyridin-3-yl-2-methyl-4-(3-(trifluoromethoxy)benzyl)piperazine-1-carboxylate Form B can be obtained from an ethyl acetate/n-heptane mixture, methyl acetate, acetone or methylene chloride.

In certain embodiments, crystalline (R)-5-carbamoylpyridin-3-yl-2-methyl-4-(3-(trifluoromethoxy)benzyl)piperazine-1-carboxylate Form B may be characterized by X-ray powder diffraction analysis.

In one embodiment, provided is crystalline (R)-5-carbamoylpyridin-3-yl-2-methyl-4-(3-(trifluoromethoxy)benzyl)piperazine-1-carboxylate Form B having an X-ray powder diffraction pattern comprising peaks at 16.2, 18.2, and 19.2 degrees 2θ+0.2 degrees 2θ.

In one embodiment, provided is crystalline (R)-5-carbamoylpyridin-3-yl-2-methyl-4-(3-(trifluoromethoxy)benzyl)piperazine-1-carboxylate Form B wherein the X-ray powder diffraction pattern further comprises peaks at 15.1, 18.7, and 20.1 degrees 2θ±0.2 degrees 2θ.

In certain embodiments, crystalline (R)-5-carbamoylpyridin-3-yl-2-methyl-4-(3-(trifluoromethoxy)benzyl)piperazine-1-carboxylate Form B is characterized by XRPD peaks located at one, two, three, four, five, six, seven, eight, nine, ten, eleven or twelve of the following approximate positions: 15.1, 16.2, 17.9, 18.2, 18.7, 19.2, 20.1, 21.1, 24.3, 25.0, 27.4, and 27.6 degrees 2θ. In certain embodiments, crystalline (R)-5-carbamoylpyridin-3-yl-2-methyl-4-(3-(trifluoromethoxy)benzyl)piperazine-1-carboxylate Form B is characterized by an XRPD pattern having 1, 2, 3, 4, 5, 6, 7, 8, 9, 10, 11, 12, 13, 14, 15, 16, 17, 18, 19, 20, 21, 22, 23, 24 or 25 peaks matching peaks in the representative XRPD pattern provided herein.

Figure 7:
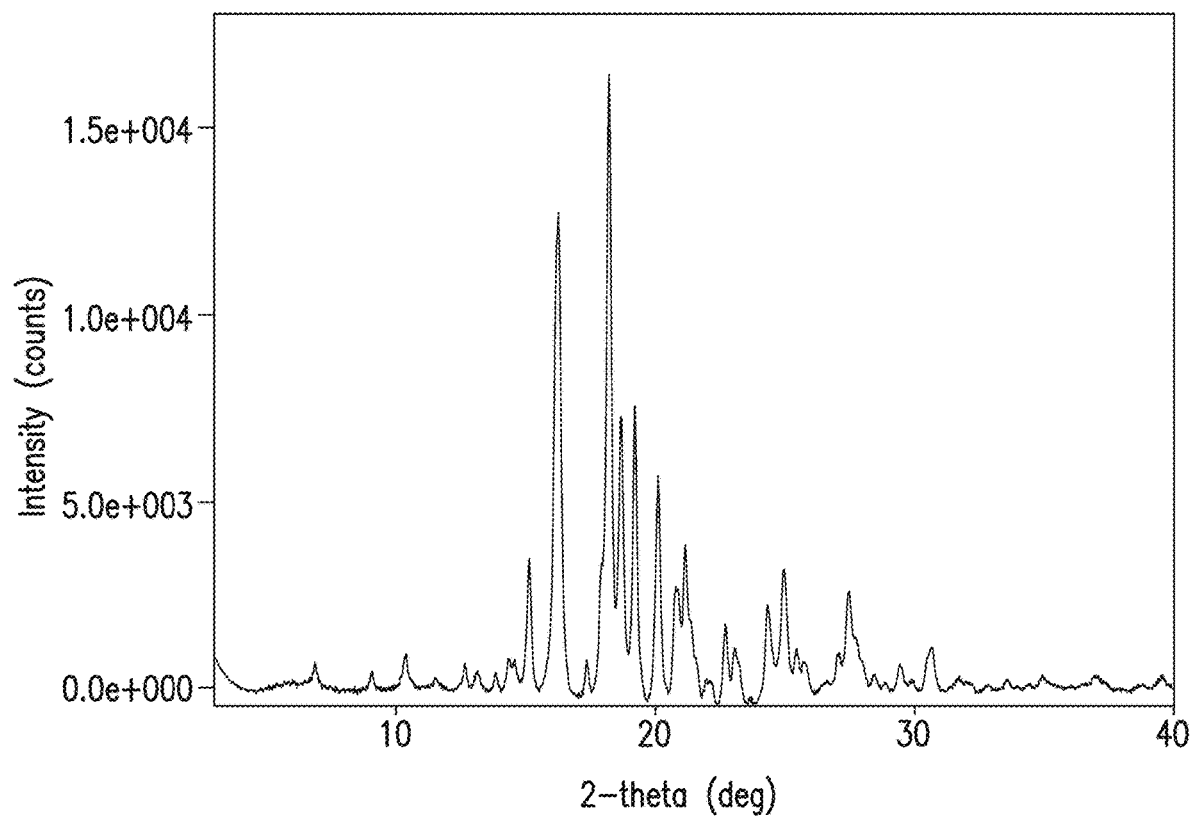
FIG. 7 provides a representative XRPD pattern of crystalline (R)-5-carbamoylpyridin-3-yl-2-methyl-4-(3-(trifluoromethoxy)benzyl)piperazine-1-carboxylate Form B.

In one embodiment, provided is crystalline (R)-5-carbamoylpyridin-3-yl-2-methyl-4-(3-(trifluoromethoxy)benzyl)piperazine-1-carboxylate Form B having an X-ray powder diffraction pattern corresponding to the representative X-ray powder diffraction patterns depicted in FIG. 7.

In certain embodiments, crystalline (R)-5-carbamoylpyridin-3-yl-2-methyl-4-(3-(trifluoromethoxy)benzyl)piperazine-1-carboxylate Form B may be characterized by thermal analysis.

In one embodiment, provided is crystalline (R)-5-carbamoylpyridin-3-yl-2-methyl-4-(3-(trifluoromethoxy)benzyl)piperazine-1-carboxylate Form B having a differential scanning calorimetry thermogram comprising an endotherm with a maximum at about 95° C.

In one embodiment, provided is crystalline (R)-5-carbamoylpyridin-3-yl-2-methyl-4-(3-(trifluoromethoxy)benzyl)piperazine-1-carboxylate Form B having a differential scanning calorimetry thermogram comprising an endotherm with an onset at about 91° C.

Figure 8:
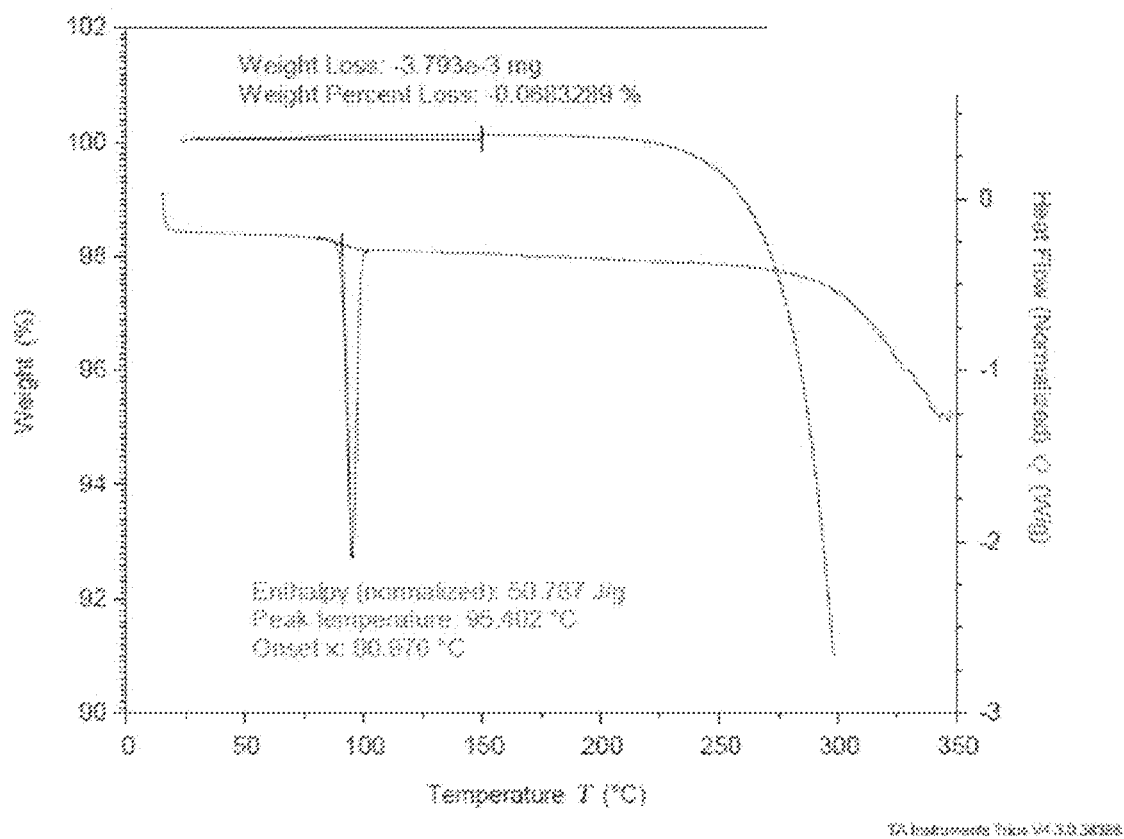
FIG. 8 provides a representative DSC thermogram and a representative TGA thermogram of crystalline (R)-5-carbamoylpyridin-3-yl-2-methyl-4-(3-(trifluoromethoxy)benzyl)piperazine-1-carboxylate Form B.

In one embodiment, provided is crystalline (R)-5-carbamoylpyridin-3-yl-2-methyl-4-(3-(trifluoromethoxy)benzyl)piperazine-1-carboxylate Form B having a differential scanning calorimetry thermogram corresponding to the representative differential scanning calorimetry thermogram depicted in FIG. 8.

In one embodiment, provided is crystalline (R)-5-carbamoylpyridin-3-yl-2-methyl-4-(3-(trifluoromethoxy)benzyl)piperazine-1-carboxylate Form B which is anhydrous.

In one embodiment, provided is crystalline (R)-5-carbamoylpyridin-3-yl-2-methyl-4-(3-(trifluoromethoxy)benzyl)piperazine-1-carboxylate Form B having a thermogravimetric analysis thermogram comprising a weight loss of less than about 2.5% when heated from about 30° C. to about 100° C.

In one embodiment, provided is crystalline (R)-5-carbamoylpyridin-3-yl-2-methyl-4-(3-(trifluoromethoxy)benzyl)piperazine-1-carboxylate Form B having a thermogravimetric analysis thermogram comprising a weight loss of less than about 1.0% when heated from about 30° C. to about 150° C.

In one embodiment, provided is crystalline (R)-5-carbamoylpyridin-3-yl-2-methyl-4-(3-(trifluoromethoxy)benzyl)piperazine-1-carboxylate Form B having a thermogravimetric analysis thermogram comprising a weight loss of less than about 0.1% when heated from about 30° C. to about 150° C.

In one embodiment, provided is crystalline (R)-5-carbamoylpyridin-3-yl-2-methyl-4-(3-(trifluoromethoxy)benzyl)piperazine-1-carboxylate Form B having a thermogravimetric analysis thermogram corresponding to the representative thermogravimetric analysis thermogram depicted in FIG. 8.

In one embodiment, provided is crystalline (R)-5-carbamoylpyridin-3-yl-2-methyl-4-(3-(trifluoromethoxy)benzyl)piperazine-1-carboxylate Form B which is substantially physically pure.

In one embodiment, provided is crystalline (R)-5-carbamoylpyridin-3-yl-2-methyl-4-(3-(trifluoromethoxy)benzyl)piperazine-1-carboxylate Form B which is substantially chemically pure.

In one embodiment, provided is a pharmaceutical composition comprising a crystalline (R)-5-carbamoylpyridin-3-yl-2-methyl-4-(3-(trifluoromethoxy)benzyl)piperazine-1-carboxylate Form B.

Certain embodiments herein provide crystalline (R)-5-carbamoylpyridin-3-yl-2-methyl-4-(3-(trifluoromethoxy)benzyl)piperazine-1-carboxylate Form C.

In one embodiment provided herein, crystalline (R)-5-carbamoylpyridin-3-yl-2-methyl-4-(3-(trifluoromethoxy)benzyl)piperazine-1-carboxylate Form C can be obtained from a 1:3 chloroform/hexane mixture. In one embodiment provided herein, crystalline (R)-5-carbamoylpyridin-3-yl-2-methyl-4-(3-(trifluoromethoxy)benzyl)piperazine-1-carboxylate can be obtained from a 1:1 ethanol/water mixture. In one embodiment provided herein, crystalline (R)-5-carbamoylpyridin-3-yl-2-methyl-4-(3-(trifluoromethoxy)benzyl)piperazine-1-carboxylate can be obtained from a 3:1 acetonitrile/water mixture. In one embodiment provided herein, crystalline (R)-5-carbamoylpyridin-3-yl-2-methyl-4-(3-(trifluoromethoxy)benzyl)piperazine-1-carboxylate can be obtained from slurrying Form B in FaSSIF. In one embodiment provided herein, crystalline (R)-5-carbamoylpyridin-3-yl-2-methyl-4-(3-(trifluoromethoxy)benzyl)piperazine-1-carboxylate can be obtained from slurrying Form B in FeSSIF.

In certain embodiments, crystalline (R)-5-carbamoylpyridin-3-yl-2-methyl-4-(3-(trifluoromethoxy)benzyl)piperazine-1-carboxylate Form C may be characterized by X-ray powder diffraction analysis.

In one embodiment, provided is crystalline (R)-5-carbamoylpyridin-3-yl-2-methyl-4-(3-(trifluoromethoxy)benzyl)piperazine-1-carboxylate Form C having an X-ray powder diffraction pattern comprising peaks at 18.0, 20.0, and 21.0 degrees 2θ±0.2 degrees 2θ.

In one embodiment, provided is crystalline (R)-5-carbamoylpyridin-3-yl-2-methyl-4-(3-(trifluoromethoxy)benzyl)piperazine-1-carboxylate Form C wherein the X-ray powder diffraction pattern further comprises peaks at 12.3, 16.8, and 25.5 degrees 2θ+0.2 degrees 2θ.

In certain embodiments, crystalline (R)-5-carbamoylpyridin-3-yl-2-methyl-4-(3-(trifluoromethoxy)benzyl)piperazine-1-carboxylate Form C is characterized by XRPD peaks located at one, two, three, four, five, six, seven, eight, nine, ten, eleven, twelve, thirteen, fourteen, fifteen, sixteen, seventeen, eighteen, nineteen, twenty, twenty-one, or twenty-two of the following approximate positions: 12.3, 14.1, 14.7, 14.8, 15.5, 15.7, 16.2, 16.8, 17.1, 18.0, 18.2, 18.5, 19.5, 20.0, 20.5, 21.0, 21.4, 22.8, 24.6, 25.5, 25.9, and 29.6 degrees 2θ. In certain embodiments, crystalline (R)-5-carbamoylpyridin-3-yl-2-methyl-4-(3-(trifluoromethoxy)benzyl)piperazine-1-carboxylate Form C is characterized by an XRPD pattern having 1, 2, 3, 4, 5, 6, 7, 8, 9, 10, 11, 12, 13, 14, 15, 16, 17, 18, 19, 20, 21, 22, 23, 24 or 25 peaks matching peaks in the representative XRPD pattern provided herein.

Figure 9:
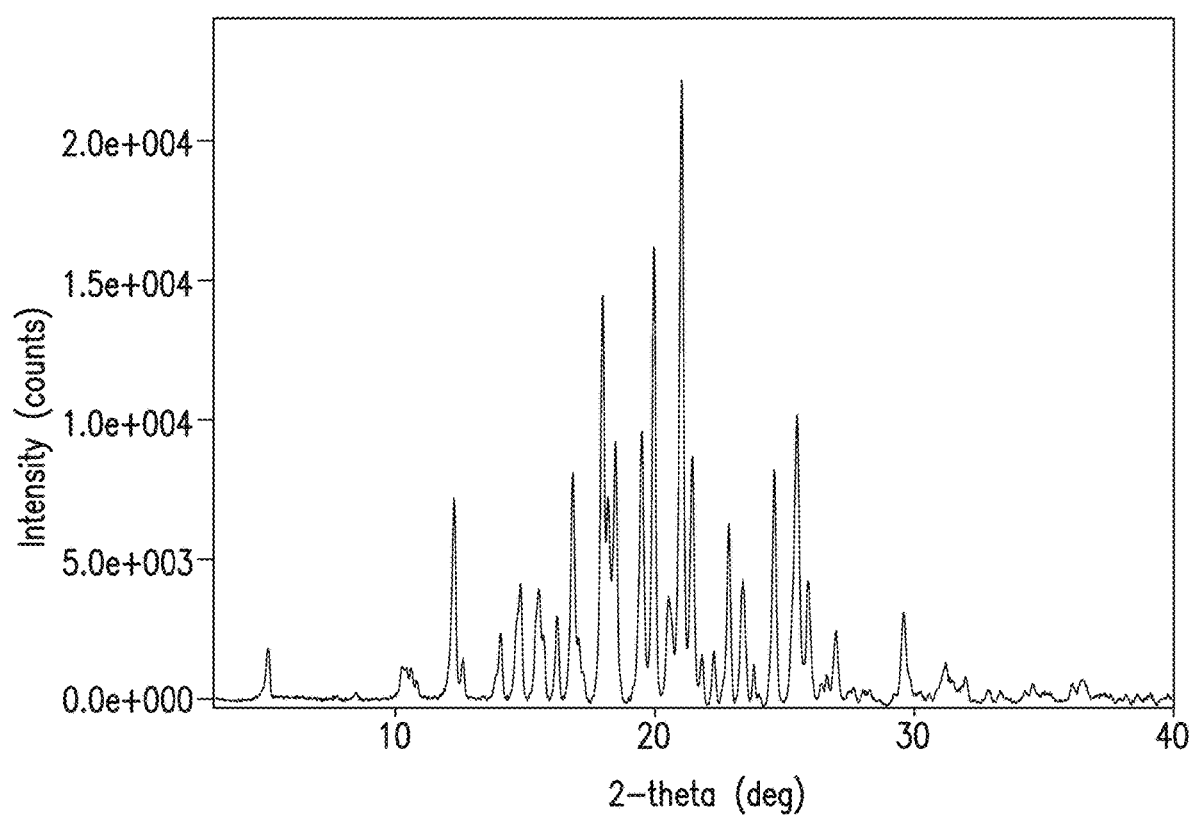
FIG. 9 provides a representative XRPD pattern of crystalline (R)-5-carbamoylpyridin-3-yl-2-methyl-4-(3-(trifluoromethoxy)benzyl)piperazine-1-carboxylate Form C.

In one embodiment, provided is crystalline (R)-5-carbamoylpyridin-3-yl-2-methyl-4-(3-(trifluoromethoxy)benzyl)piperazine-1-carboxylate Form C having an X-ray powder diffraction pattern corresponding to the representative X-ray powder diffraction patterns depicted in FIG. 9.

In certain embodiments, crystalline (R)-5-carbamoylpyridin-3-yl-2-methyl-4-(3-(trifluoromethoxy)benzyl)piperazine-1-carboxylate Form C may be characterized by thermal analysis.

In one embodiment, provided is crystalline (R)-5-carbamoylpyridin-3-yl-2-methyl-4-(3-(trifluoromethoxy)benzyl)piperazine-1-carboxylate Form C having a differential scanning calorimetry thermogram comprising an endotherm with a maximum at about 99° C.

In one embodiment, provided is crystalline (R)-5-carbamoylpyridin-3-yl-2-methyl-4-(3-(trifluoromethoxy)benzyl)piperazine-1-carboxylate Form C having a differential scanning calorimetry thermogram comprising an endotherm with an onset at about 98° C.

Figure 10:
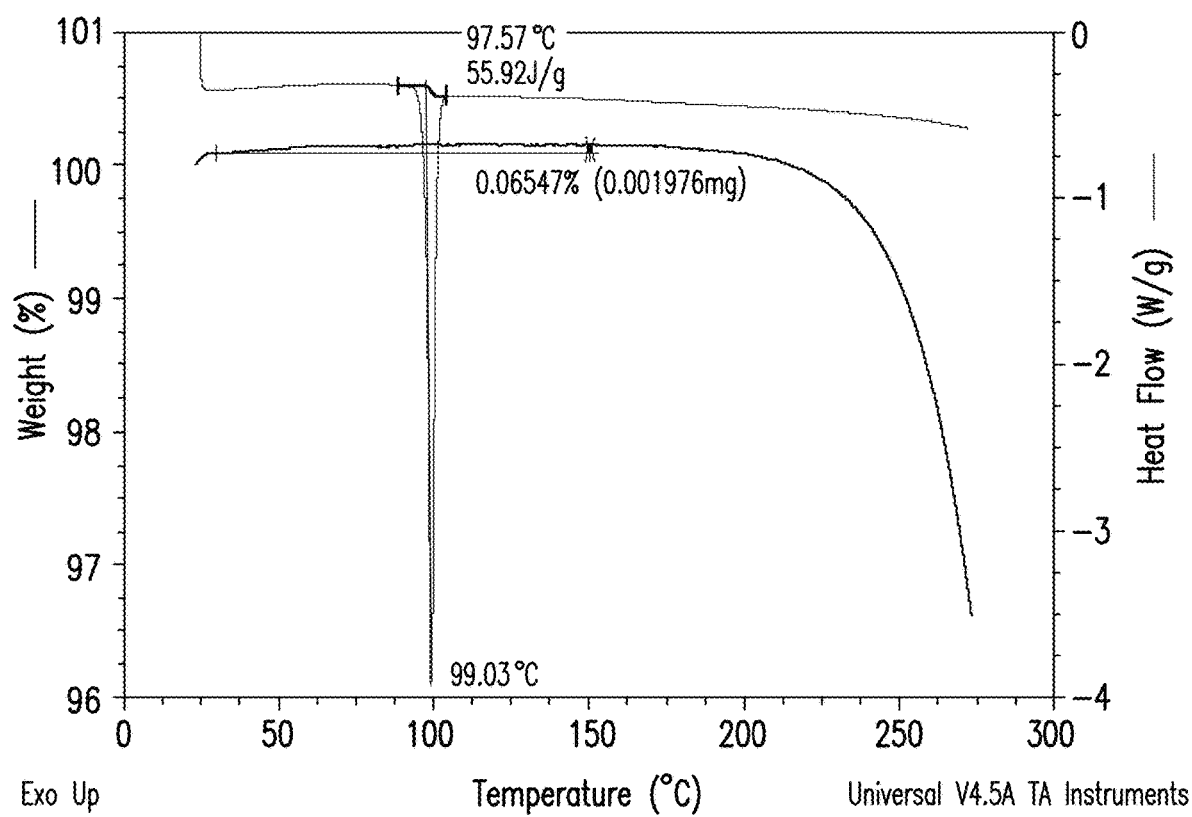
FIG. 10 provides a representative DSC thermogram and TGA thermogram of crystalline (R)-5-carbamoylpyridin-3-yl-2-methyl-4-(3-(trifluoromethoxy)benzyl)piperazine-1-carboxylate Form C.

In one embodiment, provided is crystalline (R)-5-carbamoylpyridin-3-yl-2-methyl-4-(3-(trifluoromethoxy)benzyl)piperazine-1-carboxylate Form C having a differential scanning calorimetry thermogram corresponding to the representative differential scanning calorimetry thermograms depicted in FIG. 10.

In one embodiment, provided is crystalline (R)-5-carbamoylpyridin-3-yl-2-methyl-4-(3-(trifluoromethoxy)benzyl)piperazine-1-carboxylate Form C which is anhydrous.

In one embodiment, provided is crystalline (R)-5-carbamoylpyridin-3-yl-2-methyl-4-(3-(trifluoromethoxy)benzyl)piperazine-1-carboxylate Form C having a thermogravimetric analysis thermogram comprising a weight loss of about 0.149% when heated from about 30° C. to about 150° C.

In one embodiment, provided is crystalline (R)-5-carbamoylpyridin-3-yl-2-methyl-4-(3-(trifluoromethoxy)benzyl)piperazine-1-carboxylate Form C having a thermogravimetric analysis thermogram comprising a weight loss of less than about 1.0% when heated from about 30° C. to about 150° C.

In one embodiment, provided is crystalline (R)-5-carbamoylpyridin-3-yl-2-methyl-4-(3-(trifluoromethoxy)benzyl)piperazine-1-carboxylate Form C having a thermogravimetric analysis thermogram comprising a weight loss of about 0.15% when heated from about 30° C. to about 150° C.

In one embodiment, provided is crystalline (R)-5-carbamoylpyridin-3-yl-2-methyl-4-(3-(trifluoromethoxy)benzyl)piperazine-1-carboxylate Form C having a thermogravimetric analysis thermogram corresponding to the representative thermogravimetric analysis thermogram depicted in FIG. 10.

In one embodiment, provided is crystalline (R)-5-carbamoylpyridin-3-yl-2-methyl-4-(3-(trifluoromethoxy)benzyl)piperazine-1-carboxylate Form C which is substantially physically pure.

In one embodiment, provided is crystalline (R)-5-carbamoylpyridin-3-yl-2-methyl-4-(3-(trifluoromethoxy)benzyl)piperazine-1-carboxylate Form C which is substantially chemically pure.

In one embodiment, provided is a pharmaceutical composition comprising crystalline (R)-5-carbamoylpyridin-3-yl-2-methyl-4-(3-(trifluoromethoxy)benzyl)piperazine-1-carboxylate Form C.

Certain embodiments herein provide crystalline (R)-5-carbamoylpyridin-3-yl-2-methyl-4-(3-(trifluoromethoxy)benzyl)piperazine-1-carboxylate Form D.

In one embodiment provided herein, crystalline (R)-5-carbamoylpyridin-3-yl-2-methyl-4-(3-(trifluoromethoxy)benzyl)piperazine-1-carboxylate Form D can be obtained from slurrying Form B in methyl tert-butyl ether (MTBE).

In certain embodiments, crystalline (R)-5-carbamoylpyridin-3-yl-2-methyl-4-(3-(trifluoromethoxy)benzyl)piperazine-1-carboxylate Form D may be characterized by X-ray powder diffraction analysis.

In one embodiment, provided is crystalline (R)-5-carbamoylpyridin-3-yl-2-methyl-4-(3-(trifluoromethoxy)benzyl)piperazine-1-carboxylate Form D having an X-ray powder diffraction pattern comprising peaks at 13.4, 21.0, and 23.8 degrees 2θ+0.2 degrees 2θ.

In one embodiment, provided is crystalline (R)-5-carbamoylpyridin-3-yl-2-methyl-4-(3-(trifluoromethoxy)benzyl)piperazine-1-carboxylate Form D wherein the X-ray powder diffraction pattern further comprises peaks at 18.3, 26.7, and 29.5 degrees 2θ±0.2 degrees 2θ.

In certain embodiments, crystalline (R)-5-carbamoylpyridin-3-yl-2-methyl-4-(3-(trifluoromethoxy)benzyl)piperazine-1-carboxylate Form D is characterized by XRPD peaks located at one, two, three, four, five, six, seven, eight, nine, ten, eleven, twelve, thirteen, fourteen, fifteen, sixteen, or seventeen of the following approximate positions: 13.4, 14.0, 14.8, 16.1, 16.8, 18.0, 18.3, 18.6, 19.5, 19.8, 20.7, 21.0, 22.8, 23.8, 24.4, 26.7, and 29.5 degrees 2θ. In certain embodiments, crystalline (R)-5-carbamoylpyridin-3-yl-2-methyl-4-(3-(trifluoromethoxy)benzyl)piperazine-1-carboxylate Form D is characterized by an XRPD pattern having 1, 2, 3, 4, 5, 6, 7, 8, 9, 10, 11, 12, 13, 14, 15, 16, 17, 18, 19, 20, 21, 22, 23, 24 or 25 peaks matching peaks in the representative XRPD pattern provided herein.

Figure 11:
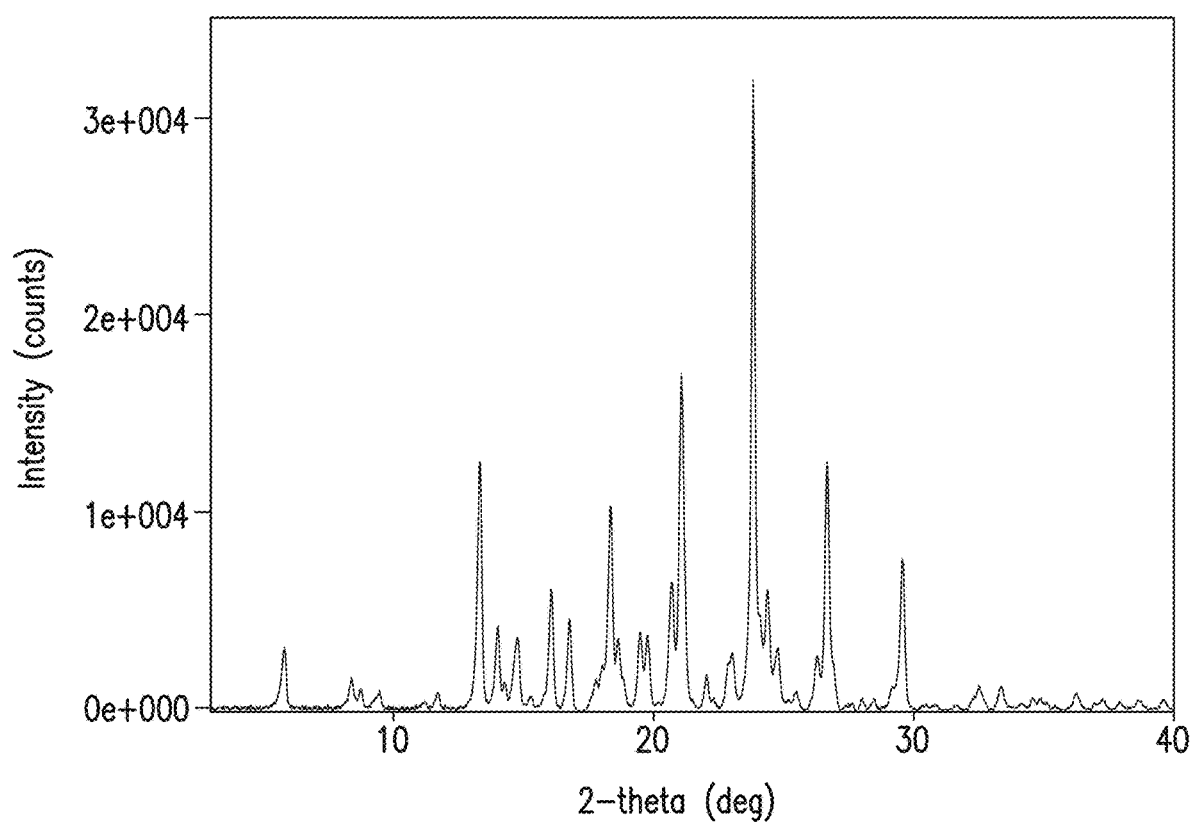
FIG. 11 provides a representative XRPD pattern of crystalline (R)-5-carbamoylpyridin-3-yl-2-methyl-4-(3-(trifluoromethoxy)benzyl)piperazine-1-carboxylate Form D.

In one embodiment, provided is crystalline (R)-5-carbamoylpyridin-3-yl-2-methyl-4-(3-(trifluoromethoxy)benzyl)piperazine-1-carboxylate Form D having an X-ray powder diffraction pattern corresponding to the representative X-ray powder diffraction patterns depicted in FIG. 11.

In certain embodiments, crystalline (R)-5-carbamoylpyridin-3-yl-2-methyl-4-(3-(trifluoromethoxy)benzyl)piperazine-1-carboxylate Form D may be characterized by thermal analysis.

In one embodiment, provided is crystalline (R)-5-carbamoylpyridin-3-yl-2-methyl-4-(3-(trifluoromethoxy)benzyl) piperazine-1-carboxylate Form D having a differential scanning calorimetry thermogram comprising an endotherm with a maximum at about 101° C.

In one embodiment, provided is crystalline (R)-5-carbamoylpyridin-3-yl-2-methyl-4-(3-(trifluoromethoxy)benzyl) piperazine-1-carboxylate Form D having a differential scanning calorimetry thermogram comprising an endotherm with an onset at about 99° C.

Figure 12:
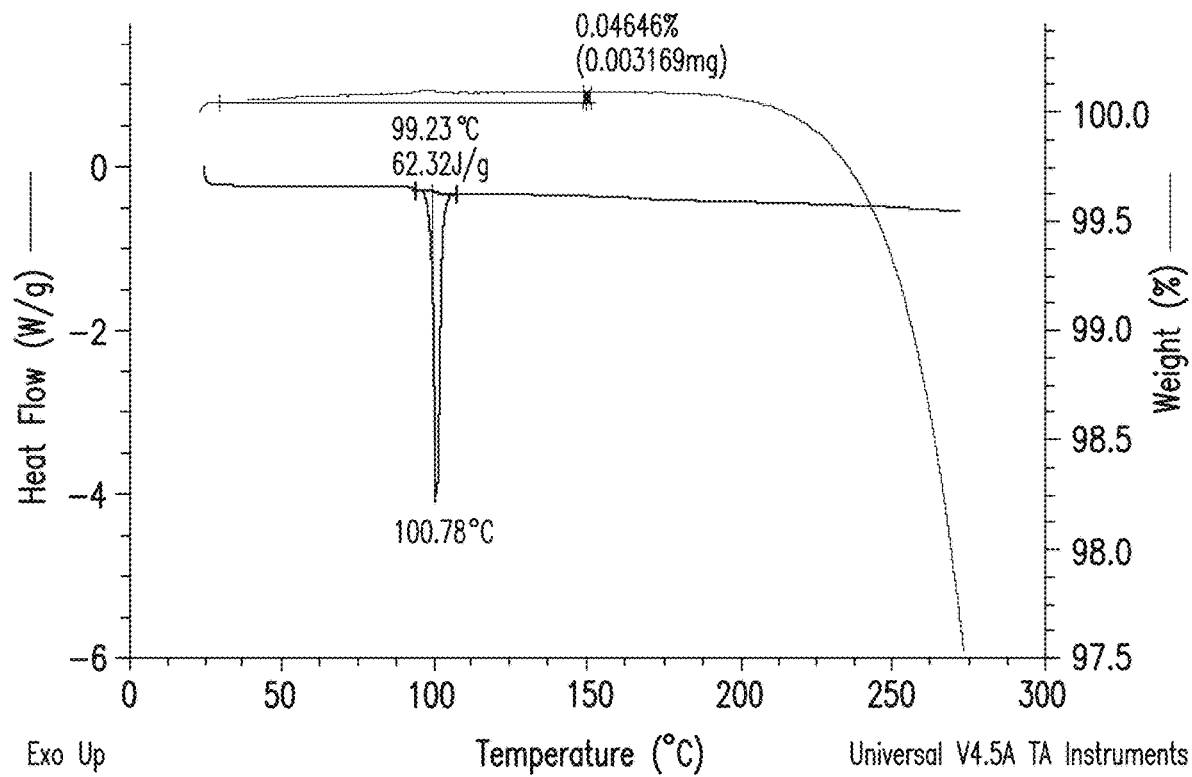
FIG. 12 provides a representative DSC thermogram and TGA thermogram of crystalline (R)-5-carbamoylpyridin-3-yl-2-methyl-4-(3-(trifluoromethoxy)benzyl)piperazine-1-carboxylate Form D.

In one embodiment, provided is crystalline (R)-5-carbamoylpyridin-3-yl-2-methyl-4-(3-(trifluoromethoxy)benzyl) piperazine-1-carboxylate Form D having a differential scanning calorimetry thermogram corresponding to the representative differential scanning calorimetry thermogram depicted in FIG. 12.

In one embodiment, provided is crystalline (R)-5-carbamoylpyridin-3-yl-2-methyl-4-(3-(trifluoromethoxy)benzyl) piperazine-1-carboxylate Form D which is anhydrous.

In one embodiment, provided is crystalline (R)-5-carbamoylpyridin-3-yl-2-methyl-4-(3-(trifluoromethoxy)benzyl) piperazine-1-carboxylate Form D having a thermogravimetric analysis thermogram comprising a weight loss of about 0.054% when heated from about 30° C. to about 150° C.

In one embodiment, provided is crystalline (R)-5-carbamoylpyridin-3-yl-2-methyl-4-(3-(trifluoromethoxy)benzyl) piperazine-1-carboxylate Form D having a thermogravimetric analysis thermogram comprising a weight loss of less than about 0.1% when heated from about 30° C. to about 150° C.

In one embodiment, provided is crystalline (R)-5-carbamoylpyridin-3-yl-2-methyl-4-(3-(trifluoromethoxy)benzyl) piperazine-1-carboxylate Form D having a thermogravimetric analysis thermogram corresponding to the representative thermogravimetric analysis thermogram depicted in FIG. 12.

In one embodiment, provided is crystalline (R)-5-carbamoylpyridin-3-yl-2-methyl-4-(3-(trifluoromethoxy)benzyl) piperazine-1-carboxylate Form D which is substantially physically pure.

In one embodiment, provided is crystalline (R)-5-carbamoylpyridin-3-yl-2-methyl-4-(3-(trifluoromethoxy)benzyl) piperazine-1-carboxylate Form D which is substantially chemically pure.

In one embodiment, provided is a pharmaceutical composition comprising crystalline (R)-5-carbamoylpyridin-3-yl-2-methyl-4-(3-(trifluoromethoxy)benzyl)piperazine-1-carboxylate Form D.

Certain embodiments herein provide crystalline (R)-5-carbamoylpyridin-3-yl-2-methyl-4-(3-(trifluoromethoxy) benzyl)piperazine-1-carboxylate Form E.

In one embodiment provided herein, crystalline (R)-5-carbamoylpyridin-3-yl-2-methyl-4-(3-(trifluoromethoxy) benzyl)piperazine-1-carboxylate Form E can be obtained from a chloroform/hexane mixture.

In certain embodiments, crystalline (R)-5-carbamoylpyridin-3-yl-2-methyl-4-(3-(trifluoromethoxy)benzyl)piperazine-1-carboxylate Form E may be characterized by X-ray powder diffraction analysis.

In one embodiment, provided is crystalline (R)-5-carbamoylpyridin-3-yl-2-methyl-4-(3-(trifluoromethoxy)benzyl) piperazine-1-carboxylate Form E having an X-ray powder diffraction pattern comprising peaks at 17.8, 21.3, and 22.8 degrees 2θ±0.2 degrees 2θ.

In one embodiment, provided is crystalline (R)-5-carbamoylpyridin-3-yl-2-methyl-4-(3-(trifluoromethoxy)benzyl) piperazine-1-carboxylate Form E wherein the X-ray powder diffraction pattern further comprises peaks at 15.8, 18.4, and 21.9 degrees 2θ±0.2 degrees 2θ.

In certain embodiments, crystalline (R)-5-carbamoylpyridin-3-yl-2-methyl-4-(3-(trifluoromethoxy)benzyl)piperazine-1-carboxylate Form E is characterized by XRPD peaks located at one, two, three, four, five, six, seven, eight, nine, ten, eleven or twelve of the following approximate positions: 10.9, 12.7, 15.8, 17.2, 17.8, 18.4, 19.7 21.3, 21.9, 22.8, 24.2, and 25.6 degrees 2θ. In certain embodiments, crystalline (R)-5-carbamoylpyridin-3-yl-2-methyl-4-(3-(trifluoromethoxy)benzyl)piperazine-1-carboxylate is characterized by an XRPD pattern having 1, 2, 3, 4, 5, 6, 7, 8, 9, 10, 11, 12, 13, 14, 15, 16, 17, 18, 19, 20, 21, 22, 23, 24 or 25 peaks matching peaks in the representative XRPD pattern provided herein.

Figure 13:
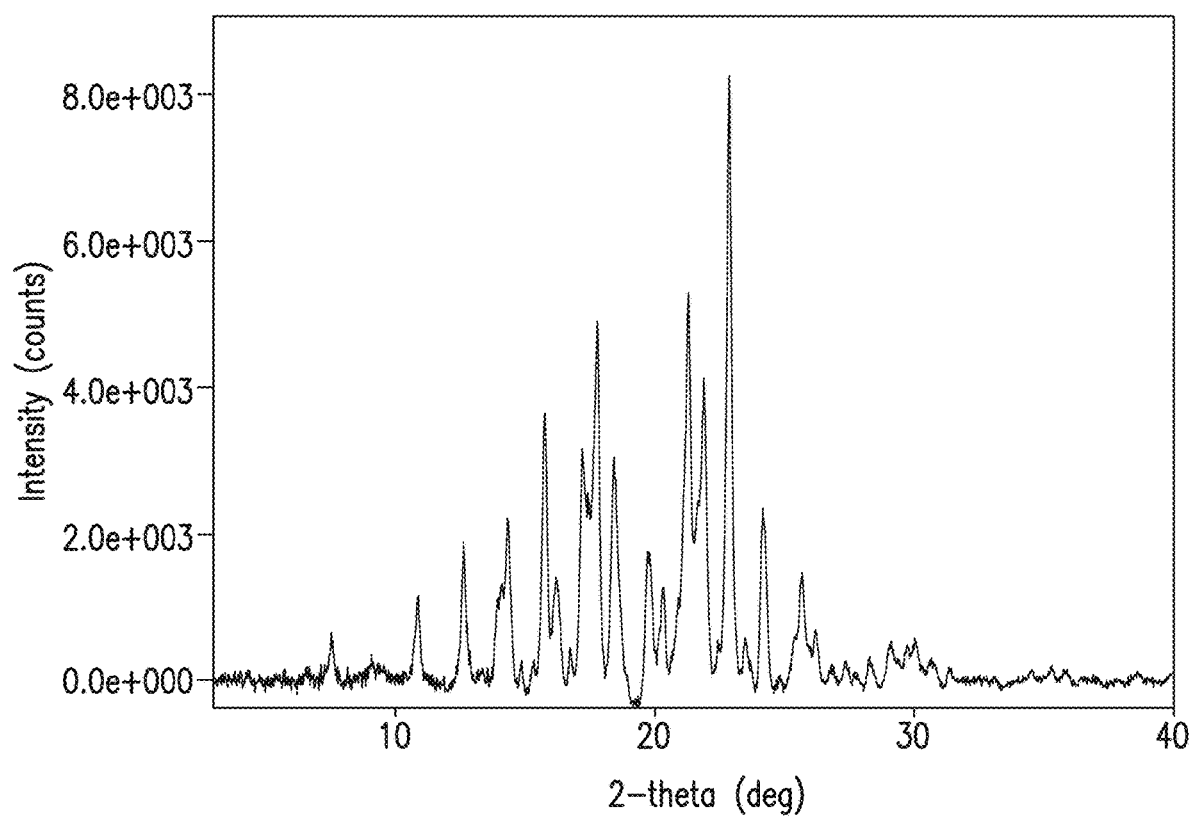
FIG. 13 provides a representative XRPD pattern of crystalline (R)-5-carbamoylpyridin-3-yl-2-methyl-4-(3-(trifluoromethoxy)benzyl)piperazine-1-carboxylate Form E.

In one embodiment, provided is crystalline (R)-5-carbamoylpyridin-3-yl-2-methyl-4-(3-(trifluoromethoxy)benzyl) piperazine-1-carboxylate Form E having an X-ray powder diffraction pattern corresponding to the representative X-ray powder diffraction patterns depicted in FIG. 13.

In certain embodiments, crystalline (R)-5-carbamoylpyridin-3-yl-2-methyl-4-(3-(trifluoromethoxy)benzyl)piperazine-1-carboxylate Form E may be characterized by thermal analysis.

In one embodiment, provided is crystalline (R)-5-carbamoylpyridin-3-yl-2-methyl-4-(3-(trifluoromethoxy)benzyl) piperazine-1-carboxylate Form E having a differential scanning calorimetry thermogram comprising an endotherm with a maximum at about 104° C.

In one embodiment, provided is crystalline (R)-5-carbamoylpyridin-3-yl-2-methyl-4-(3-(trifluoromethoxy)benzyl) piperazine-1-carboxylate Form E having a differential scanning calorimetry thermogram comprising an endotherm with an onset at about 102° C.

Figure 14:
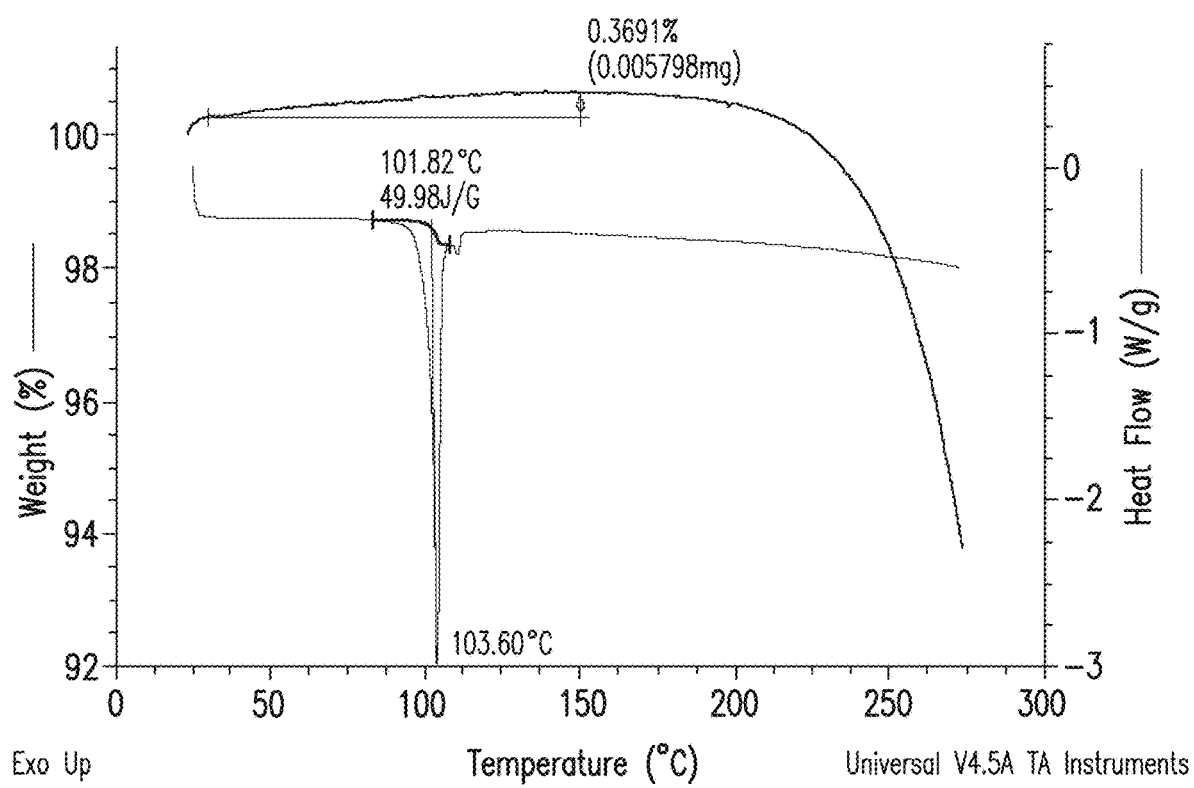
FIG. 14 provides a representative DSC thermogram and TGA thermogram of crystalline (R)-5-carbamoylpyridin-3-yl-2-methyl-4-(3-(trifluoromethoxy)benzyl)piperazine-1-carboxylate Form E.

In one embodiment, provided is crystalline (R)-5-carbamoylpyridin-3-yl-2-methyl-4-(3-(trifluoromethoxy)benzyl) piperazine-1-carboxylate Form E having a differential scanning calorimetry thermogram corresponding to the representative differential scanning calorimetry thermograms depicted in FIG. 14.

In one embodiment, provided is crystalline (R)-5-carbamoylpyridin-3-yl-2-methyl-4-(3-(trifluoromethoxy)benzyl) piperazine-1-carboxylate Form E which is anhydrous.

In one embodiment, provided is crystalline (R)-5-carbamoylpyridin-3-yl-2-methyl-4-(3-(trifluoromethoxy)benzyl) piperazine-1-carboxylate Form E having a thermogravimetric analysis thermogram comprising a weight loss of about 0.37% when heated from about 30° C. to about 150° C.

In one embodiment, provided is crystalline (R)-5-carbamoylpyridin-3-yl-2-methyl-4-(3-(trifluoromethoxy)benzyl) piperazine-1-carboxylate Form E having a thermogravimetric analysis thermogram comprising a weight loss of less than about 1.0% when heated from about 30° C. to about 150° C.

In one embodiment, provided is crystalline (R)-5-carbamoylpyridin-3-yl-2-methyl-4-(3-(trifluoromethoxy)benzyl) piperazine-1-carboxylate Form E having a thermogravimetric analysis thermogram corresponding to the representative thermogravimetric analysis thermogram depicted in FIG. 14.

In one embodiment, provided is crystalline (R)-5-carbamoylpyridin-3-yl-2-methyl-4-(3-(trifluoromethoxy)benzyl)piperazine-1-carboxylate Form E which is substantially physically pure.

In one embodiment, provided is crystalline (R)-5-carbamoylpyridin-3-yl-2-methyl-4-(3-(trifluoromethoxy)benzyl)piperazine-1-carboxylate Form E which is substantially chemically pure.

In one embodiment, provided is a pharmaceutical composition comprising crystalline (R)-5-carbamoylpyridin-3-yl-2-methyl-4-(3-(trifluoromethoxy)benzyl)piperazine-1-carboxylate Form E.

Pharmaceutical Compositions

Pharmaceutical compositions and single unit dosage forms comprising crystalline forms of (R)-5-carbamoylpyridin-3-yl-2-methyl-4-(3-(trifluoromethoxy)benzyl)piperazine-1-carboxylate are provided herein. Also provided herein are methods for preparing pharmaceutical compositions and single unit dosage forms comprising crystalline forms of (R)-5-carbamoylpyridin-3-yl-2-methyl-4-(3-(trifluoromethoxy)benzyl)piperazine-1-carboxylate. For example, in certain embodiments, individual dosage forms comprising crystalline (R)-5-carbamoylpyridin-3-yl-2-methyl-4-(3-(trifluoromethoxy)benzyl)piperazine-1-carboxylate provided herein or prepared using crystalline forms of (R)-5-carbamoylpyridin-3-yl-2-methyl-4-(3-(trifluoromethoxy)benzyl)piperazine-1-carboxylate provided herein may be suitable for oral, mucosal (including rectal, nasal, or vaginal), parenteral (including subcutaneous, intramuscular, bolus injection, intraarterial, or intravenous), sublingual, transdermal, buccal, or topical administration.

In certain embodiments, pharmaceutical compositions and dosage forms provided herein comprise crystalline forms of (R)-5-carbamoylpyridin-3-yl-2-methyl-4-(3-(trifluoromethoxy)benzyl)piperazine-1-carboxylate. Certain embodiments herein provide pharmaceutical compositions and dosage forms comprising crystalline form of (R)-5-carbamoylpyridin-3-yl-2-methyl-4-(3-(trifluoromethoxy)benzyl)piperazine-1-carboxylate, wherein the crystalline form of (R)-5-carbamoylpyridin-3-yl-2-methyl-4-(3-(trifluoromethoxy)benzyl)piperazine-1-carboxylate is substantially pure. Certain embodiments herein provide pharmaceutical compositions and dosage forms comprising crystalline form of (R)-5-carbamoylpyridin-3-yl-2-methyl-4-(3-(trifluoromethoxy)benzyl)piperazine-1-carboxylate as provided herein, which is substantially free of other crystalline solid forms of (R)-5-carbamoylpyridin-3-yl-2-methyl-4-(3-(trifluoromethoxy)benzyl)piperazine-1-carboxylate and/or amorphous solid forms of (R)-5-carbamoylpyridin-3-yl-2-methyl-4-(3-(trifluoromethoxy)benzyl)piperazine-1-carboxylate. Pharmaceutical compositions and dosage forms provided herein typically also comprise one or more pharmaceutically acceptable excipients, diluents or carriers.

Single unit dosage forms provided herein are suitable for oral or parenteral (e.g., subcutaneous, intravenous, bolus injection, intramuscular, or intraarterial) administration to a patient. Examples of dosage forms include, but are not limited to: tablets; caplets; capsules, such as soft elastic gelatin capsules; powders and sterile solids that can be reconstituted to provide liquid dosage forms suitable for parenteral administration to a patient.

The composition, shape, and type of dosage forms provided herein will typically vary depending on their use. A parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., *Remington's Pharmaceutical Sciences,* 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form.

Like the amounts and types of excipients, the amounts and specific types of active ingredients in a dosage form may differ depending on factors such as, but not limited to, the route by which it is to be administered to patients. However, typical dosage forms provided herein lie within the range of from about 0.1 mg to about 1,000 mg per day, given as a single once-a-day dose in the morning or as divided doses throughout the day. More specifically, the daily dose may be administered twice, three times, or four times daily in equally divided doses. Specifically, a daily dose range may be from about 0.1 mg to about 500 mg per day, more specifically, between about 0.1 mg and about 200 mg per day. A daily dose range may be 1 mg, 2 mg, 3 mg, 4 mg, or 5 mg. In managing the patient, the therapy may be initiated at a lower dose, perhaps about 1 mg to about 25 mg, and increased if necessary up to about 200 mg to about 1,000 mg per day as either a single dose or divided doses, depending on the patient's global response.

Oral Dosage Forms

Pharmaceutical compositions provided herein that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally Remington's Pharmaceutical Sciences, 18th ed., Mack Publishing, Easton Pa. (1990).

Typical oral dosage forms provided herein are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101™, AVICEL-PH-103™, AVICEL RC-581™, AVICEL-PH-105™ (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-58 ™. Suitable anhydrous or low moisture excipients or additives include AVICEL-PH-103™ and Starch 1500 LM™.

Disintegrants are used in the compositions provided herein to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms provided herein include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms provided herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200™, manufactured by W.R. Grace Co. of Baltimore, Md.), a coagulated aerosol of synthetic silica (marketed by Degussa Co. of Plano, Tex.), CAB-O-SIL™ (a pyrogenic silicon dioxide product sold by Cabot Co. of Boston, Mass.), and mixtures thereof. If used at all, lubricants are typically used in an amount of less than about one weight percent of the pharmaceutical compositions or dosage forms into which they are incorporated.

Parenteral Dosage Forms

Parenteral dosage forms can be administered to patients by various routes including, but not limited to, subcutaneous, intravenous (including bolus injection), intramuscular, and intraarterial injection. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms provided herein are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol, and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms provided herein.

Combination Treatment

Also contemplated herein are combination therapies, for example, co-administering a disclosed compound and an additional active agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually weeks, months, or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration is accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent is effected by any appropriate route including, but not limited to, oral routes, intravenous routes, intramuscular routes, and direct absorption through mucous membrane tissues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally or all therapeutic agents are administered by intravenous injection.

Combination therapy also embraces the administration of the therapeutic agents as described above in further combination with other biologically active ingredients and non-drug therapies. Where the combination therapy further comprises a non-drug treatment, the non-drug treatment is conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as conventional oral dosage forms, that are administered either simultaneously or sequentially.

For example, e.g., for contemplated treatment of pain, a disclosed compound is co-administered with another therapeutic for pain such as an opioid, a cannabinoid receptor (CB-1 or CB-2) modulator, a COX-2 inhibitor, acetaminophen, and/or a non-steroidal anti-inflammatory agent. Additional therapeutics e.g., for the treatment of pain that are co-administered, include morphine, codeine, hydromorphone, hydrocodone, oxymorphone, fentanyl, tramadol, and levorphanol.

Other contemplated therapeutics for co-administration include aspirin, naproxen, ibuprofen, salsalate, diflunisal, dexibuprofen, fenoprofen, ketoprofen, oxaprozin, loxoprofen, indomethacin, tolmetin, sulindac, etodolac, ketorolac, piroxicam, meloxicam, tenoxicam, droxicam, lornoxicam, celecoxib, parecoxib, rimonabant, and/or etoricoxib.

EXAMPLES

Example 1: (R)-5-carbamoylpyridin-3-yl-2-methyl-4-(3-(trifluoromethoxy)benzyl)piperazine-1-carboxylate Form A Form A was obtained with several solvents, including methanol, isopropyl acetate, and a 9:1 mixture of ethanol/water. Form A was also prepared by slurrying starting material (a mixture of Form A/C) in toluene at RT for 1 day. NMR spectra of Form A indicates trace amount of surface toluene. HPLC purity of Form A sample was measured to be 99.87 area %. Form A has a differential scanning calorimetry thermogram comprising an endotherm with an onset of about 111-112° C. and a maximum at about 113° C. (shown in FIG. 2). Form A has a thermogravimetric analysis thermogram comprising a weight loss of less than about 0.1% when heated from about 30° C. to about 100° C., indicating anhydrous material (shown in FIG. 2).

Figure 3:
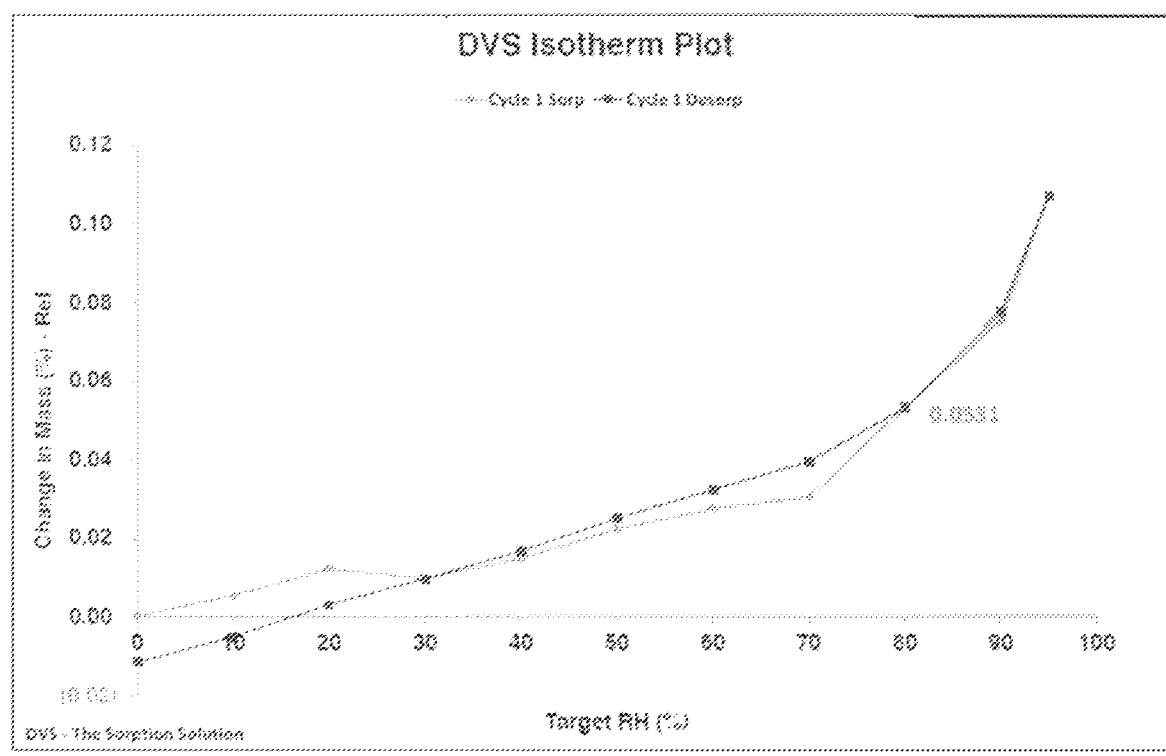
FIG. 3 provides a representative dynamic vapor sorption (DVS) plot of crystalline (R)-5-carbamoylpyridin-3-yl-2-methyl-4-(3-(trifluoromethoxy)benzyl)piperazine-1-carboxylate Form A.
Figure 4:
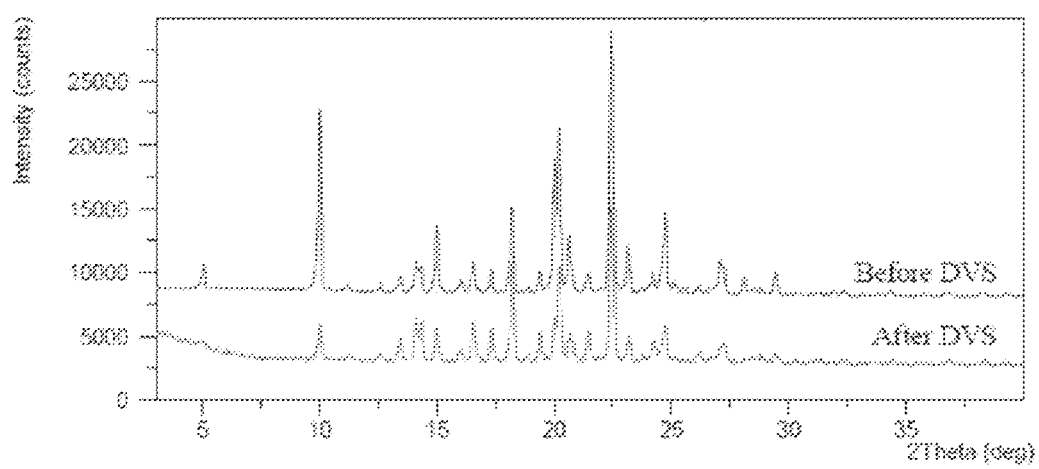
FIG. 4 provides representative XRPD patterns of crystalline (R)-5-carbamoylpyridin-3-yl-2-methyl-4-(3-(trifluoromethoxy)benzyl)piperazine-1-carboxylate Form A before and after a DVS experiment.

The dynamic vapor sorption (DVS) isotherm plot of Form A was collected at 25° C. between 0 and 95% RH (shown in FIG. 3). A water uptake of 0.05% was observed at 25° C./80% RH. The XRPD comparison indicated that no form change was observed for Form A after the DVS test (shown in FIG. 4).

Figure 5:
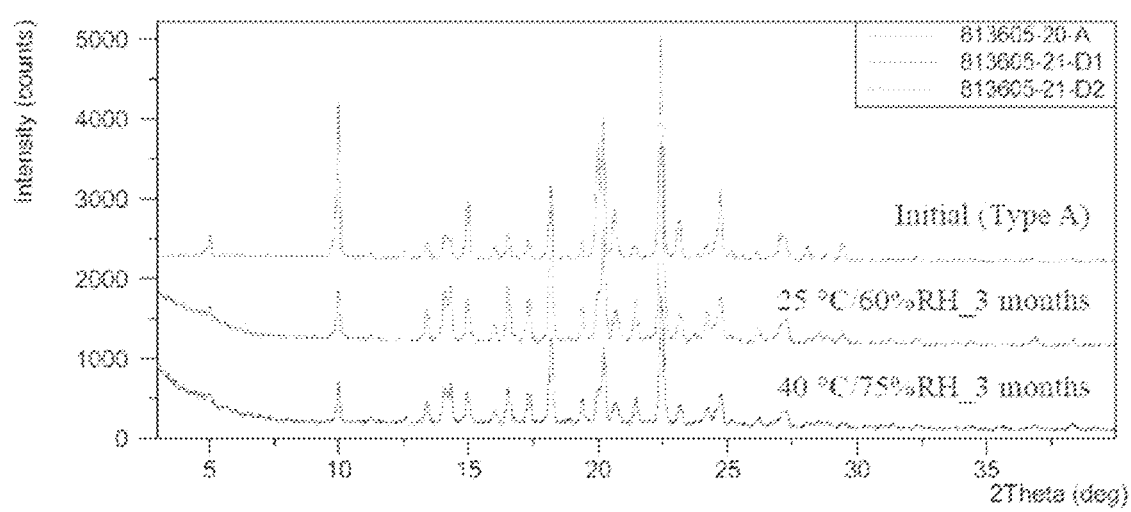
FIG. 5 provides representative XRPD patterns of crystalline (R)-5-carbamoylpyridin-3-yl-2-methyl-4-(3-(trifluoromethoxy)benzyl)piperazine-1-carboxylate Form A before and after accelerated conditions stability tests.
Figure 6:
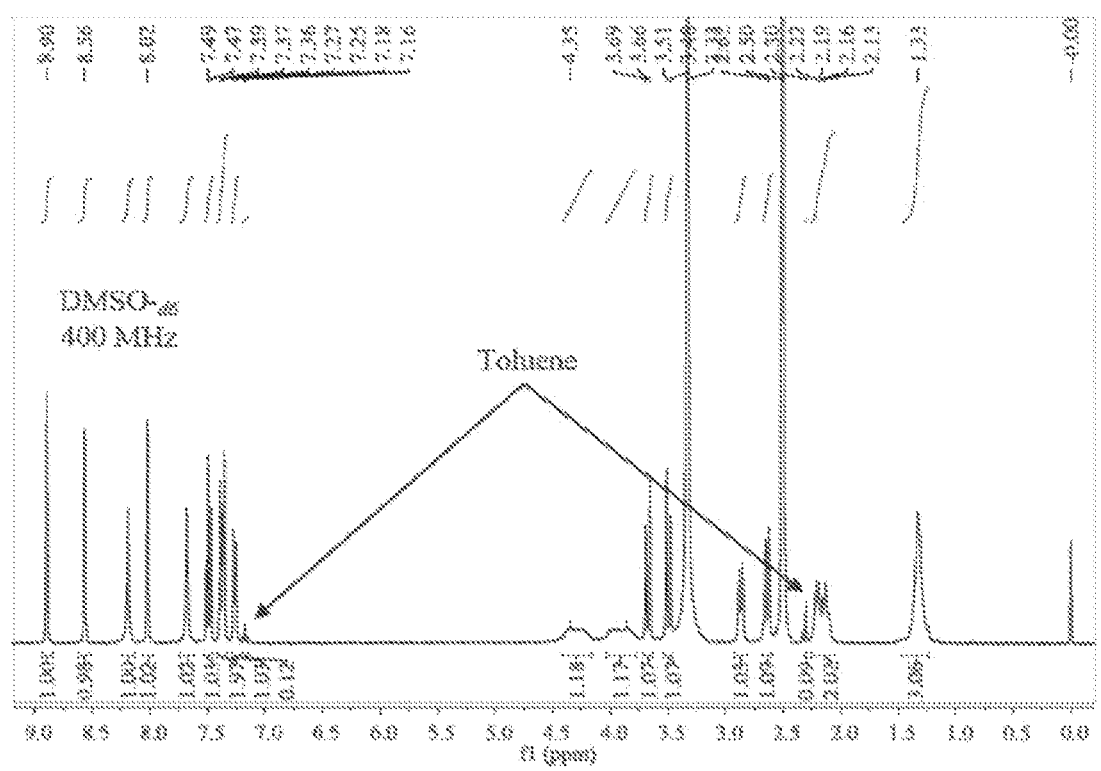
FIG. 6 provides a representative nuclear magnetic resonance (NMR) spectrum of crystalline (R)-5-carbamoylpyridin-3-yl-2-methyl-4-(3-(trifluoromethoxy)benzyl)piperazine-1-carboxylate Form A.

Form A sample showed good physical and chemical stability under accelerated conditions of 25° C./60% RH and 40° C./75% RH for 3 months. X-ray powder diffractograms comparing Form A before and after accelerated conditions is shown in FIG. 5. XRPD peaks for Form A are shown in Tables 1 and 2 (different XRPD instruments and samples; peaks below a certain amplitude are omitted for clarity).

TABLE 1

XRPD peaks of Form A.

| No. | 2-theta(deg) | d(ang.) | Height(counts) |
|---|---|---|---|
| 1 | 4.9 | 17.85 | 445 |
| 2 | 9.9 | 8.906 | 7062 |
| 3 | 12.5 | 7.086 | 450 |
| 4 | 13.4 | 6.625 | 1881 |
| 5 | 14.0 | 6.324 | 3185 |
| 6 | 14.2 | 6.212 | 3613 |
| 7 | 14.9 | 5.934 | 4377 |
| 8 | 16.0 | 5.545 | 1117 |
| 9 | 16.5 | 5.378 | 3668 |
| 10 | 16.7 | 5.302 | 461 |
| 11 | 17.3 | 5.131 | 2862 |
| 12 | 18.1 | 4.888 | 10138 |
| 13 | 18.8 | 4.721 | 543 |
| 14 | 19.3 | 4.589 | 2757 |
| 15 | 19.7 | 4.50 | 561 |
| 16 | 19.9 | 4.449 | 6638 |
| 17 | 20.1 | 4.405 | 12550 |
| 18 | 20.6 | 4.311 | 3593 |
| 19 | 21.4 | 4.151 | 2679 |
| 20 | 22.3 | 3.975 | 21984 |
| 21 | 23.1 | 3.851 | 3116 |
| 22 | 24.1 | 3.684 | 1875 |
| 23 | 24.7 | 3.605 | 4728 |
| 24 | 25.1 | 3.551 | 636 |
| 25 | 26.1 | 3.415 | 947 |
| 26 | 27.0 | 3.301 | 2208 |
| 27 | 27.2 | 3.279 | 2457 |
| 28 | 28.0 | 3.185 | 852 |
| 29 | 28.8 | 3.100 | 535 |
| 30 | 29.3 | 3.041 | 1477 |
| 31 | 31.2 | 2.863 | 536 |
| 32 | 32.2 | 2.777 | 594 |
| 33 | 34.3 | 2.615 | 457 |
| 34 | 36.7 | 2.446 | 592 |
| 35 | 38.2 | 2.352 | 607 |

TABLE 2

XRPD peaks of Form A.

| No. | 2-theta(deg) | d(ang.) | Height(counts) |
|---|---|---|---|
| 1 | 4.9 | 17.85 | 445 |
| 2 | 9.9 | 8.906 | 7062 |
| 3 | 12.5 | 7.086 | 450 |
| 4 | 13.4 | 6.625 | 1881 |
| 5 | 14.0 | 6.324 | 3185 |
| 6 | 14.2 | 6.212 | 3613 |
| 7 | 14.9 | 5.934 | 4377 |
| 8 | 16.0 | 5.545 | 1117 |
| 9 | 16.5 | 5.378 | 3668 |
| 10 | 16.7 | 5.302 | 461 |

TABLE 2-continued

XRPD peaks of Form A.

| No. | 2-theta(deg) | d(ang.) | Height(counts) |
|---|---|---|---|
| 11 | 17.3 | 5.131 | 2862 |
| 12 | 18.1 | 4.888 | 10138 |
| 13 | 18.8 | 4.721 | 543 |
| 14 | 19.3 | 4.589 | 2757 |
| 15 | 19.7 | 4.50 | 561 |
| 16 | 19.9 | 4.449 | 6638 |
| 17 | 20.1 | 4.405 | 12550 |
| 18 | 20.6 | 4.311 | 3593 |
| 19 | 21.4 | 4.151 | 2679 |
| 20 | 22.3 | 3.975 | 21984 |
| 21 | 23.1 | 3.851 | 3116 |
| 22 | 24.1 | 3.684 | 1875 |
| 23 | 24.7 | 3.605 | 4728 |
| 24 | 25.1 | 3.551 | 636 |
| 25 | 26.1 | 3.415 | 947 |
| 26 | 27.0 | 3.301 | 2208 |
| 27 | 27.2 | 3.279 | 2457 |
| 28 | 28.0 | 3.185 | 852 |
| 29 | 28.8 | 3.100 | 535 |
| 30 | 29.3 | 3.041 | 1477 |
| 31 | 31.2 | 2.863 | 536 |
| 32 | 32.2 | 2.777 | 594 |
| 33 | 34.3 | 2.615 | 457 |
| 34 | 36.7 | 2.446 | 592 |
| 35 | 38.2 | 2.352 | 607 |

Example 2: (R)-5-carbamoylpyridin-3-yl-2-methyl-4-(3-(trifluoromethoxy)benzyl)piperazine-1-carboxylate Form B Form B was obtained with a 9:1 mixture of acetonitrile/water. Form B was also obtained via liquid vapor diffusion from mixture of ethyl acetate/n-heptane as well as evaporation in neat methyl acetate, acetone, or methylene chloride. The XRPD peaks for Form B are displayed in Table 3. A weight loss of less than 1.0% was observed when heated from about 30° C. to about 100° C. The DSC result exhibited a sharp endotherm onset at 91° C. and an endotherm with a maximum at about 95° C. Based on the low TGA weight loss and the single sharp DSC endotherm, Form B was postulated to be an anhydrate.

TABLE 3

XRPD peaks of Form B.

| No. | 2-theta(deg) | d(ang.) | Height(counts) |
|---|---|---|---|
| 1 | 6.9 | 12.86 | 341 |
| 2 | 9.1 | 9.74 | 232 |
| 3 | 10.4 | 8.522 | 563 |
| 4 | 11.5 | 7.700 | 142 |
| 5 | 12.7 | 6.985 | 359 |
| 6 | 13.1 | 6.730 | 257 |
| 7 | 13.8 | 6.39 | 273 |
| 8 | 14.3 | 6.182 | 473 |
| 9 | 15.1 | 5.847 | 2206 |
| 10 | 16.2 | 5.465 | 8503 |
| 11 | 17.3 | 5.114 | 551 |
| 12 | 17.9 | 4.950 | 2243 |
| 13 | 18.2 | 4.871 | 9600 |
| 14 | 18.7 | 4.754 | 4314 |
| 15 | 19.2 | 4.619 | 4926 |
| 16 | 20.1 | 4.421 | 3639 |
| 17 | 20.7 | 4.289 | 859 |
| 18 | 20.8 | 4.262 | 1649 |
| 19 | 21.1 | 4.205 | 2422 |
| 20 | 21.3 | 4.165 | 1181 |
| 21 | 21.6 | 4.120 | 421 |
| 22 | 22.7 | 3.922 | 1134 |

TABLE 3-continued

XRPD peaks of Form B.

| No. | 2-theta(deg) | d(ang.) | Height(counts) |
|---|---|---|---|
| 23 | 23.0 | 3.861 | 720 |
| 24 | 24.3 | 3.661 | 1424 |
| 25 | 25.0 | 3.566 | 2080 |
| 26 | 25.4 | 3.498 | 525 |
| 27 | 25.8 | 3.458 | 460 |
| 28 | 27.0 | 3.301 | 568 |
| 29 | 27.4 | 3.252 | 1417 |
| 30 | 27.6 | 3.224 | 827 |
| 31 | 28.4 | 3.143 | 238 |
| 32 | 29.4 | 3.036 | 402 |
| 33 | 29.9 | 2.991 | 128 |
| 34 | 30.6 | 2.924 | 715 |
| 35 | 31.7 | 2.823 | 129 |
| 36 | 33.5 | 2.673 | 139 |
| 37 | 34.8 | 2.575 | 198 |
| 38 | 37.0 | 2.431 | 179 |
| 39 | 39.5 | 2.282 | 190 |

Example 3: (R)-5-carbamoylpyridin-3-yl-2-methyl-4-(3-(trifluoromethoxy)benzyl)piperazine-1-carboxylate Form C Form C was obtained when Form B was slurried in FaSSIF-v2 or FeSSIF-v2 at 37° C. for 2 hr. Form C can also be obtained with a 1:3 chloroform/hexane mixture. The DSC shows an endotherm with a maximum at about 99° C., and the TGA shows a weight loss of less than about 0.15% when heated from about 30° C. to about 150° C., indicating Form C is an anhydrate. XRPD peaks for Form C are shown in Table 4.

TABLE 4

XRPD peaks of Form C.

| No. | 2-theta(deg) | d(ang.) | Height(counts) |
|---|---|---|---|
| 1 | 5.1 | 17.18 | 1235 |
| 2 | 8.5 | 10.42 | 146 |
| 3 | 10.2 | 8.633 | 661 |
| 4 | 10.4 | 8.463 | 402 |
| 5 | 10.6 | 8.340 | 697 |
| 6 | 10.8 | 8.179 | 426 |
| 7 | 12.3 | 7.209 | 4781 |
| 8 | 12.6 | 7.007 | 943 |
| 9 | 14.1 | 6.294 | 1700 |
| 10 | 14.7 | 6.021 | 1871 |
| 11 | 14.8 | 5.963 | 2174 |
| 12 | 15.4 | 5.747 | 691 |
| 13 | 15.5 | 5.699 | 2577 |
| 14 | 15.7 | 5.628 | 1504 |
| 15 | 16.2 | 5.452 | 2030 |
| 16 | 16.8 | 5.259 | 5422 |
| 17 | 17.1 | 5.194 | 1475 |
| 18 | 17.3 | 5.135 | 611 |
| 19 | 18.0 | 4.928 | 9698 |
| 20 | 18.2 | 4.876 | 4834 |
| 21 | 18.5 | 4.798 | 6212 |
| 22 | 18.7 | 4.752 | 576 |
| 23 | 19.5 | 4.551 | 6357 |
| 24 | 20.0 | 4.444 | 11680 |
| 25 | 20.5 | 4.333 | 2281 |
| 26 | 21.0 | 4.223 | 15490 |
| 27 | 21.4 | 4.144 | 6064 |
| 28 | 21.8 | 4.070 | 1064 |
| 29 | 22.2 | 3.994 | 1216 |
| 30 | 22.8 | 3.893 | 4382 |
| 31 | 23.3 | 3.808 | 2959 |
| 32 | 23.8 | 3.736 | 989 |

TABLE 4-continued

XRPD peaks of Form C.

| No. | 2-theta(deg) | d(ang.) | Height(counts) |
|---|---|---|---|
| 33 | 24.6 | 3.616 | 5533 |
| 34 | 25.5 | 3.490 | 6853 |
| 35 | 25.9 | 3.434 | 3080 |
| 36 | 26.4 | 3.375 | 372 |
| 37 | 26.6 | 3.348 | 605 |
| 38 | 27.0 | 3.305 | 1594 |
| 39 | 27.6 | 3.226 | 229 |
| 40 | 28.0 | 3.186 | 201 |
| 41 | 28.2 | 3.159 | 248 |
| 42 | 29.6 | 3.019 | 2177 |
| 43 | 31.2 | 2.868 | 498 |
| 44 | 31.3 | 2.852 | 398 |
| 45 | 32.0 | 2.797 | 477 |
| 46 | 32.8 | 2.728 | 299 |
| 47 | 33.3 | 2.692 | 205 |
| 48 | 34.2 | 2.621 | 165 |
| 49 | 34.5 | 2.598 | 269 |
| 50 | 36.0 | 2.490 | 417 |
| 51 | 36.5 | 2.462 | 472 |
| 52 | 37.2 | 2.418 | 92 |

Example 4: (R)-5-carbamoylpyridin-3-yl-2-methyl-4-(3-(trifluoromethoxy)benzyl)piperazine-1-carboxylate Form D Form D can be obtained from slurrying Form B in MTBE at room temperature for 10 days. The DSC shows an endotherm with a maximum at about 101° C., and the TGA shows a weight loss of about 0.054% when heated from about 30° C. to about 150° C., indicating Form D is an anhydrate. XRPD peaks for Form D are shown in Table 5.

TABLE 5

XRPD peaks of Form D.

| No. | 2-theta(deg) | d(ang.) | Height (counts) |
|---|---|---|---|
| 1 | 5.9 | 15.094 | 2047 |
| 2 | 8.4 | 10.530 | 900 |
| 3 | 8.8 | 10.088 | 630 |
| 4 | 9.5 | 9.323 | 538 |
| 5 | 11.7 | 7.558 | 498 |
| 6 | 13.4 | 6.625 | 8528 |
| 7 | 14.0 | 6.305 | 2653 |
| 8 | 14.3 | 6.183 | 716 |
| 9 | 14.8 | 5.985 | 2408 |
| 10 | 15.3 | 5.794 | 365 |
| 11 | 16.1 | 5.510 | 4141 |
| 12 | 16.8 | 5.284 | 2986 |
| 13 | 17.8 | 4.981 | 907 |
| 14 | 18.0 | 4.924 | 1322 |
| 15 | 18.3 | 4.831 | 6368 |
| 16 | 18.6 | 4.762 | 2087 |
| 17 | 18.8 | 4.707 | 634 |
| 18 | 19.5 | 4.553 | 2557 |
| 19 | 19.8 | 4.488 | 2428 |
| 20 | 20.7 | 4.291 | 4145 |
| 21 | 21.0 | 4.218 | 11450 |
| 22 | 22.0 | 4.033 | 1042 |
| 23 | 22.8 | 3.893 | 1266 |
| 24 | 23.0 | 3.859 | 1217 |
| 25 | 23.8 | 3.734 | 23683 |
| 26 | 24.4 | 3.643 | 3299 |
| 27 | 24.8 | 3.588 | 1917 |
| 28 | 25.5 | 3.491 | 514 |
| 29 | 26.3 | 3.389 | 1610 |
| 30 | 26.7 | 3.341 | 8142 |
| 31 | 26.9 | 3.313 | 1471 |
| 32 | 28.0 | 3.187 | 402 |
| 33 | 29.5 | 3.021 | 5758 |
| 34 | 32.5 | 2.755 | 965 |
| 35 | 33.3 | 2.688 | 774 |
| 36 | 34.1 | 2.630 | 168 |
| 37 | 34.5 | 2.597 | 409 |
| 38 | 34.8 | 2.577 | 418 |
| 39 | 35.0 | 2.560 | 253 |
| 40 | 36.2 | 2.480 | 555 |
| 41 | 36.9 | 2.433 | 224 |
| 42 | 37.2 | 2.413 | 319 |
| 43 | 37.8 | 2.376 | 248 |
| 44 | 38.6 | 2.329 | 294 |
| 45 | 39.6 | 2.276 | 359 |

Example 5: (R)-5-carbamoylpyridin-3-yl-2-methyl-4-(3-(trifluoromethoxy)benzyl)piperazine-1-carboxylate Form E Form E can be obtained from slurring Form C in a chloroform/hexane mixture at rt for 9 days. The DSC shows an endotherm with a maximum at about 104° C., and the TGA shows a weight loss of about 0.37% when heated from about 30° C. to about 150° C., indicating Form E is an anhydrate. XRPD peaks for Form E are shown in Table 6.

TABLE 6

XRPD peaks for Form E.

| No. | 2-theta(deg) | d(ang.) | Height (counts) |
|---|---|---|---|
| 1 | 7.5 | 11.73 | 333 |
| 2 | 9.1 | 9.71 | 115 |
| 3 | 10.9 | 8.144 | 698 |
| 4 | 12.7 | 7.006 | 1164 |
| 5 | 14.0 | 6.327 | 793 |
| 6 | 14.3 | 6.173 | 1113 |
| 7 | 15.8 | 5.622 | 2425 |
| 8 | 16.2 | 5.462 | 915 |
| 9 | 16.8 | 5.279 | 274 |
| 10 | 17.2 | 5.158 | 1845 |
| 11 | 17.8 | 4.985 | 2556 |
| 12 | 18.4 | 4.818 | 1879 |
| 13 | 19.7 | 4.502 | 1215 |
| 14 | 20.3 | 4.371 | 778 |
| 15 | 21.3 | 4.167 | 2749 |
| 16 | 21.9 | 4.054 | 2304 |
| 17 | 22.7 | 3.923 | 377 |
| 18 | 22.8 | 3.892 | 5540 |
| 19 | 23.5 | 3.790 | 358 |
| 20 | 24.2 | 3.681 | 1614 |
| 21 | 25.4 | 3.511 | 392 |
| 22 | 25.6 | 3.475 | 839 |
| 23 | 26.2 | 3.399 | 398 |
| 24 | 27.3 | 3.264 | 171 |
| 25 | 28.3 | 3.156 | 237 |
| 26 | 29.0 | 3.075 | 342 |
| 27 | 29.7 | 3.007 | 278 |
| 28 | 30.0 | 2.975 | 310 |
| 29 | 30.7 | 2.910 | 151 |

Example 6: Stability and Solubility Tests

A solution stability test of Form A was performed to assess substantial degradation of (R)-5-carbamoylpyridin-3-yl-2-methyl-4-(3-(trifluoromethoxy)benzyl)piperazine-1- carboxylate in physiologically relevant media. A solution of (R)-5-carbamoylpyridin-3-yl-2-methyl-4-(3-(trifluoromethoxy)benzyl)piperazine-1-carboxylate (1 mg/mL) was prepared in acetonitrile/water (50/50 v/v). Test medium (1990 µL) was added to a vial. Test media evaluated included buffers pH 1-8, simulated gastric fluid (SGF), fasted state simulated intestinal fluid (FaSSIF), and fed state simulated intestinal fluid (FeSSIF). Stock solution (10 µL) was added to the vial containing the medium. This mixture was stirred to mix well and transferred to a HPLC vial, which was placed in the autosampler maintained at 37° C. The vial was injected repeatedly every 4 hr for 24 hr. Results are shown in Table 7. Solubility is shown in Table 8.

TABLE 7

Solution chemical stability data for crystalline (R)-5-carbamoylpyridin-3-yl-2-methyl-4-(3-(trifluoromethoxy)benzyl)piperazine-1-carboxylate Form A at 37° C.

| Time (hr) | pH = 1 | pH = 3 | pH = 5.0 | pH = 6.8 | pH = 8.0 | SGF | FaSSIF | FeSSIF |
|---|---|---|---|---|---|---|---|---|
| 0 | 100.0 | 100.0 | 100.0 | 100.0 | 100.0 | 100.0 | 100.0 | 100.0 |
| 4 | 99.6 | 99.8 | 100.9 | 100.2 | 101.3 | 100.2 | 100.6 | 99.6 |
| 8 | 100.3 | 99.8 | 101.7 | 100.8 | 100.5 | 100.1 | 100.2 | 100.2 |
| 12 | 100.3 | 98.5 | 99.9 | 100.1 | 99.7 | 99.2 | 100.5 | 99.7 |
| 16 | 99.9 | 99.3 | 100.7 | 100.0 | 100.1 | 99.7 | 100.3 | 99.6 |
| 20 | 101.9 | 99.6 | 99.9 | 99.6 | 98.7 | 100.4 | 100.0 | 99.8 |
| 24 | 100.5 | 99.5 | 99.6 | 99.0 | 99.4 | 99.6 | 100.0 | 99.7 |

TABLE 8

Solubility of crystalline (R)-5-carbamoylpyridin-3-yl-2-methyl-4-(3-(trifluoromethoxy)benzyl)piperazine-1-carboxylate Form A in physiologically relevant media (37° C.).

| Medium | Final Measured pH | Solubility (mg/mL)* |
|---|---|---|
| pH 1.0 HCl/NaCl buffer | 1.47 | >20 |
| pH 2.5 Phosphate buffer | 3.44 | 4.326 |
| pH 3 Phosphae buffer | 4.20 | 1.251 |
| pH 4 Acetate buffer | 4.18 | 0.696 |
| pH 5 Acetate buffer | 5.14 | 0.091 |
| pH 6.8 Phosphate buffer | 6.88 | 0.007 |
| pH 8.0 Phosphate buffer | 8.10 | 0.005 |
| SGF with pepsin | 1.75 | >20 |
| FaSSIF | 6.48 | 0.146 |
| FeSSIF | 5.17 | 1.018 |
| pH 1 (0.1N HCl) | 1.48 | >20 |
| pH 2 (0.01N HCl) | 3.55 | 3.858 |
| pH 3 (0.001N HCl) | 4.90 | 0.057 |
| pH 4 (0.0001N HCl) | 7.78 | 0.011 |
| Water | 8.10 | 0.012 |

Example 7: Stress Polymorph Screen

A stress polymorph screen using Form B as the starting form was performed. The tests were performed at room temperature or lower in a variety of solvents. Results are shown in Table 9.

TABLE 9

Stress Polymorph Screen Using Form B as the Starting Form at room temperature or lower.

| Experiment | Solvent | Temp. | State | Result |
|---|---|---|---|---|
| 1 | Ethyl Acetate | Room* | Slurry | Form A |
| 2 | Isopropyl Acetate | Room | Slurry | Form A |
| 3 | Acetone | 4° C. | Evaporation | Form B |
| 4 | Dichloromethane | 4° C. | Evaporation | Form B |
| 5 | Acetonitrile | Room* | Slurry | Form A |
| 6 | 2-Me THF | 4° C. | Evaporation | Form A |
| 7 | H$_2$O/MeOH 1/3 (v\v) Aw~0.5 | Room* | Slurry | Form A |
| 8 | H$_2$O/MeCN 1/3 (v/v) Aw~0.9 | 4° C. | Evaporation | Mainly Form C |
| 9 | MTBE | Room | Slurry | Form D |
| 10 | EtOH | Room* | Slurry | Form A |
| 11 | 2-Propanol | Room* | Slurry | Form A |
| 12 | Nitromethane | Room* | Slurry | Form A |
| 13 | H$_2$O | Room | Slurry | Form A |
| 14 | DMSO drops dispersed into water | Room | Slurry | Form B |

*Clear solution observed initially; continued stirring @ 4° C. for 1 day followed by RT for 9 days Example 8: Polymorph Screen Polymorph screening at 5° C. was performed. A solution starting with Form B was prepared in a concentration of about 50 mg in 100 to 300 µL of solvents listed in Table 10. The solution was stirred at 50° C. for 24 h.

TABLE 10

Polymorph Screening at 50° C.

| Condition | State | Result |
|---|---|---|
| H$_2$O | Slurry | Form A |
| MTBE | Slurry | Form A |
| CPME | Clear solution | Evaporation clear film only |

Example 9: Lyophilization Study

Attempts were made to generate amorphous material by lyophilizing Form B. Form B was lyophilized with a LyoSys 3 freeze dryer, in DPD core area at −40¹° C. overnight. Results are shown Table 11.

TABLE 11

Lyophilization attempts.

| Experiment | Form/Solvent | Result |
|---|---|---|
| 1 | 240 mg Form B in~4:1 $H_2O$:MeCN | Form A |
| 2 | 240 mg Form B in~3:2 $H_2O$:MeCN | Form B |
| 3 | 240 mg Form B in~2:1 $H_2O$:MeCN | Form B |

Example 10: Form A Solubility Study

Solubility was evaluated at 2 hr and 24 hr for Form A in FaSSIF-v2 and FeSSIF-v2 at 37° C. Approximately 40 mg of Form A sample was added in 2.0 mL of corresponding bio-medium to form a suspension, followed by shaking at 500 rpm at 37° C. After 2 hr and 24 hr, the supernatants were isolated by centrifugation (7000 rpm for 5 min) followed by filtration through 0.45 mm PTFE membrane and were tested by HPLC concentration and pH. The residual solids were characterized by XRPD. As summarized in Table 12, the 24 hr solubility of Form A in FaSSIF-v2 and FeSSIF-v2 was measured to be 0.063 and 1.1 mg/mL, respectively. The XRPD patterns indicated that no form change was observed after solubility evaluation.

TABLE 12

Summary of solubility evaluation for Form A at 37° C.

| Medium | Time point (hr) | Solubility (mg/mL) | Observation | Final Form | Final pH |
|---|---|---|---|---|---|
| FaSSIF (pH 6.5) | 2 | 0.063 | Turbid | Form A | 6.5 |
| FaSSIF (pH 6.5) | 24 | 0.063 | Turbid | Form A | 6.6 |
| FeSSIF (pH 5.8) | 2 | 1.0 | Turbid | Form A | 5.9 |
| FeSSIF (pH 5.8) | 24 | 1.1 | Turbid | Form A | 6.0 |

Example 11: Accelerated Solid-State Stability Study of Form A

Solid-state stability evaluation (accelerated conditions) was performed on Form A under conditions of 25° C./60% RH and 40° C./75% RH. The detailed procedure utilized for stability evaluation is listed below:
1) weigh approximately 30 mg of Form A sample into each 3-mL vial;
2) cover the vial with Parafilm® and poke 15 holes on the Parafilm® with a needle;
3) put the vial in a stability chamber of 25° C./60% RH or 40° C./75% RH; and
4) sample for XRPD, TGA, DSC, HPLC purity and assay tests after 2, 4 and 6 weeks and 3 months.

The results of solid-state stability evaluation are summarized in Table 13. The impurities are summarized in Table 14. Based on XRPD, TGA, and DSC characterization results, no significant form change or HPLC purity decrease was observed after 3 months at both conditions. Therefore, Form A sample showed good physical and chemical stability under 25° C./60% RH and 40° C./75% RH conditions for 3 months.

TABLE 13

Stability results summary.

| Time point | Condition | Crystal form | TGA weight loss (%, up to 100° C.) | DSC endotherm | HPLC Purity (area %) | Assay vs. 5° C. control (%) |
|---|---|---|---|---|---|---|
| Initial | — | Form A | 1.2 | 110.9 | 99.86 | NA |
| 2 weeks | 25° C./60% RH | Form A | 1.1 | 110.1 | 99.84 | 101.2 |
|  | 40° C./75%/RH | Form A | 1.1 | 110.5 | 99.78 | 98.1 |
| 4 weeks | 25° C./60% RH | Form A | 1.7 | 110.9 | 99.86 | 101.4 |
|  | 40° C./75%/RH | Form A | 1.9 | 110.8 | 99.86 | 101.3 |
| 6 weeks | 25° C./60% RH | Form A | 0.2 | 110.4 | 99.86 | 99.7 |
|  | 40° C./75%/RH | Form A | 0.8 | 110.8 | 99.86 | 99.2 |

| Time point | Condition | Crystal form | TGA weight loss (%, up to 100° C.) | DSC endotherm | HPLC Purity (area %) | Assay vs. 5° C. control (%) | Chiral Purity |
|---|---|---|---|---|---|---|---|
| Initial | NA | Form A | 1.2 | 110.9 | 99.86 | NA | 100* |
| 3 months | 25° C./60% RH | Form A | 0.03 | 112.6 | 99.86 | 97.3 | 100 |
|  | 40° C./75% RH | Form A | 0.01 | 112.9 | 99.86 | 96.9 | 100 |

*The chiral purity was tested for the starting material after stored at −20° C. for about 3 months

TABLE 14

% Area of impurities summary in solid-state stability study,.

| Time point | Condition | Imp.1 (RRT 0.81) | API (RRT 1.00) | Imp.2 (RRT 1.04) | Imp.3 (RRT 1.74) |
|---|---|---|---|---|---|
| | | % Area | | | |
| Initial | NA | 0.09 | 99.86 | — | 0.05 |
| 2 weeks | 25° C./60% RH | 0.07 | 99.84 | — | 0.09 |
| | 40° C./75% RH | 0.08 | 99.78 | 0.07 | 0.07 |
| 4 weeks | 25° C./60% RH | 0.07 | 99.86 | — | 0.07 |
| | 40° C./75% RH | 0.07 | 99.86 | — | 0.07 |
| 6 weeks | 25° C./60% RH | 0.07 | 99.86 | — | 0.07 |
| | 40° C./75% RH | 0.07 | 99.86 | — | 0.07 |

| Time point | Condition | Imp.1 (RRT 0.81) | API (RRT 1.00) | Imp.3 (RRT 1.74) |
|---|---|---|---|---|
| | | % Area | | |
| Initial | NA | 0.09 | 99.86 | 0.05 |
| 3 months | 25° C./60% RH | 0.09 | 99.86 | 0.05 |
| | 40° C./75% RH | 0.09 | 99.86 | 0.05 |

—: <0.05.

Example 12: Solid State Characterization of Form A

A summary of baseline solid state characterization results of crystalline (R)-5-carbamoylpyridin-3-yl-2-methyl-4-(3-(trifluoromethoxy)benzyl)piperazine-1-carboxylate Form A, including pKa, partition coefficient (log D7.4) measurement and 2-hrs equilibrium solubility in FaSSIF and FeSSIF (version 2) are provided herein. All results obtained are summarized in Table 15. The pKa values were first predicted by Marvin® and then detected by Sirius T3 with the range from 2.0 to 12.0 (in triplicate). Log D7.4 was measured with the solvent system of pH 7.4 phosphate buffer and n-octanol by shake-flask method. Meanwhile, 2-hrs equilibrium solubility of (R)-5-carbamoylpyridin-3-yl-2-methyl-4-(3-(trifluoromethoxy)benzyl)piperazine-1-carboxylate in FaSSIF and FeSSIF (version 2) was measured to be 0.12 and 0.080 mg/mL.

TABLE 15

Summary of pKa, Log D and solubility results.

| pKa | | | 2-Hrs equilibrium solubility (mg/mL) | |
|---|---|---|---|---|
| Predicted pKa value | Measured pKa value | Log D$_{7.4}$ | FaSSIF | FeSSIF |
| 2.26, 6.67 | 5.79 | 3.76 | 0.12 | 0.080 | pKa values were predicted and detected in the range of 2.0 to 12.0
N/A: no measurement.

Example 13: Solubility of Form A

Approximate solubility of Form A was determined in 20 solvent systems at RT. Approximately 2 mg of sample was added into a 3-mL glass vial. Solvents in Table 16 were then added stepwise (100 μL per step) into the vials until the solids were dissolved visually or a total volume of 2 mL was reached. Solubility results summarized in Table 16 were used to guide the solvent selection in screening experiment design.

TABLE 16

Approximate solubility of Form A at RT

| Solvent | Solubility (mg/mL) | Solvent | Solubility (mg/mL) |
|---|---|---|---|
| MeOH | S > 73.0 | 1,4-dioxane | S > 22.0 |
| EtOH | S > 17.0 | DCM | S > 19.0 |
| IPA | S > 24.0 | CHCl$_3$ | S > 19.0 |
| Acetone | S > 17.0 | ACN | S > 24.0 |
| MIBK | S > 24.0 | Anisole | S > 20.0 |
| EtOAc | S > 26.0 | toluene | 4.5 < S < 6.0 |
| IPAc | S > 21.0 | n-heptane | S < 0.9 |
| MTBE | 7.7 < S < 11.5 | NMP | S > 21.0 |
| THF | S > 26.0 | DMSO | S > 20.0 |
| 2-MeTHF | S > 23.0 | H$_2$O | S > 1.0 |

Example 14: Solubility of Form B

Solubility of Form B was evaluated at 2 hr for Form B in FaSSIF-v2 and FeSSIF-v2 at 37° C. Approximately 10 to 20 mg of Form B sample was added in 0.8 mL of corresponding bio-relevant medium to form a suspension, followed by shaking at 500 rpm at 37° C. After 2 hr, the supernatants were isolated by centrifugation (7200 rpm for 5 min) followed by filtration through 0.45 mm PTFE membrane and were tested by HPLC concentration and pH. The residual solids were characterized by XRPD. As summarized in Table 17, Form B converted to a new form (Form C) after solubility evaluation, while the solubility in FaSSIF-v2 and FeSSIF-v2 was measured to be 0.12 and 0.080 mg/mL, respectively.

TABLE 17

Summary of solubility evaluation for storm B at 37° C.

| Medium | Time point (hr) | Solubility (mg/mL) | Observation | Final Form | Final pH |
|---|---|---|---|---|---|
| FaSSIF (pH 6.5) | 2 | 0.12 | Turbid | Form C | 6.6 |
| FeSSIF (pH 5.8) | 2 | 0.08 | Turbid | Form C | 5.9 |

Approximately 55 to 90 mg of Form B was added into a 4 mL glass vial. Solvent list in Table 18 was added into each of the vial. These samples were stirred for 3 minutes prior to visual solubility assessment.

TABLE 18

Summary of solubility evaluation for Form B at room temperature.

| | | |
|---|---|---|
| 1 | Ethyl Acetate | >800 mg/mL |
| 2 | Isopropyl Acetate | <810 mg/mL |
| 3 | Acetone | >430 mg/mL |
| 4 | Dichloromethane | >830 mg/mL |
| 5 | Acetonitrile | >720 mg/mL |
| 6 | 2-Me THF | >810 mg/mL |
| 7 | $H_2O$/MeOH 1/3 (v/v) Aw~0.5 | >780 mg/mL |
| 8 | $H_2O$/MeCN 1/3 (v/v) Aw~0.9 | >730 mg/mL |
| 10 | EtOH | >800 mg/mL |
| 11 | 2-Propanol | >365 mg/mL |
| 12 | Nitromethane | >560 mg/mL |

Example 15: Anti-Solvent Addition Experiments

Anti-solvent addition experiments were performed. A total of 8 anti-solvent addition experiments were carried out. Approximately 15 mg of Form A was dissolved in 0.5 mL solvent to obtain a clear solution, and the solution was magnetically stirred, followed by the addition of the anti-solvent to induce precipitation until the total amount of anti-solvent reached 10 mL. The precipitate was isolated for XRPD analysis. Clear solutions were transferred to −20° C. for 5 hr. Results summarized in Table 19 showed that only Form A was obtained.

TABLE 19

Summary of anti-solvent addition experiments

| Solvent | Anti-solvent | Solid Form |
|---|---|---|
| EtOH | $H_2O$ | Form A* |
| 1,4-dioxane | | Form A |
| DMSO | | Form A |
| THF | | Form A |
| EtOAc | n-heptane | Form A |
| $CHCl_3$ | | Form A* |
| Acetone | | Form A* |
| THF | | Form A* |

*These solids were obtained by slurry at −20° C.

Example 16: Slow Evaporation Experiments

Slow evaporation experiments were performed under 6 conditions. Approximately 15 mg of Form A was dissolved in 1.0 mL of corresponding solvent in a 3-mL glass vial. The visually clear solutions were evaporated at RT to induce precipitation. The solids were isolated for XRPD analysis. Results summarized in Table 20 indicated that Form A, Form B, and amorphous were obtained.

TABLE 20

Summary of slow evaporation experiments.

| Solvent (v/v) | Solid Form |
|---|---|
| MeOH | Form A |
| IPAc | Form A |
| 2-MeTHF | Amorphous |
| ACN | Amorphous |
| EtOH:$H_2O$ (9:1) | Form A |
| ACN:$H_2O$ (9:1) | Form B |

Example 17: Slow Cooling Experiments

Slow cooling experiments were conducted in 2 solvent systems. Approximately 50 mg of Form A was suspended in 0.5~1.0 mL of solvent in a 3-mL glass vial at RT. The suspension was then heated to 50° C., equilibrated for about 2 hr and filtered into a new vial. Filtrates were slowly cooled down to 5° C. at a rate of 0.1° C./min. Clear solutions were transferred to −20° C., followed by evaporation to dryness at RT and then solids were tested by XRPD. Results summarized in Table 21 indicated only Form A was obtained.

TABLE 21

Summary of slow cooling experiments

| Solvent (v/v) | Solid Form |
|---|---|
| MTBE/EtOAc (9:1) | Form A* |
| Toluene/EtOH (9:1) | Form A* |

*: These solids were obtained by evaporation at RT

Example 18: Slurry Conversion Experiments

Slurry conversion experiments were performed. Slurry conversion experiments were conducted at RT in 7 different solvent systems. Approximately 20 mg of Form A was suspended in 0.3~0.9 mL of solvent in a HPLC glass vial. After the suspensions were stirred for 5 days at RT, the remaining solids were isolated for XRPD analysis. Clear solutions were obtained after stirring, in which anti-solvent of n-heptane was added to induce crystallization. Results summarized in Table 22 indicated that only Form A was obtained.

TABLE 22

Summary of slurry conversion experiments at RT.

| Solvent (v/v) | Solid Form |
|---|---|
| MTBE | Form A |
| Toluene | Form A |
| Acetone/n-heptane (1:2) | Form A |
| THF/n-heptane (1:2) | Form A* |
| 1,4-dioxane/$H_2O$ (1:2) | Form A |
| IPA/$H_2O$ (937/63, aw~0.5) | Form A |
| $H_2O$ | Form A |

*: Solids were obtained after anti-solvent addition of n-heptane

Slurry conversion experiments were also conducted at 50° C. in 3 different solvent systems. Approximately 20 mg of Form A was suspended in 0.4~1.0 mL of solvent in a HPLC glass vial. After the suspensions were stirred for 5 days at 50° C., the remaining solids were isolated for XRPD analysis. Clear solutions were obtained after stirring, in which anti-solvent of n-heptane was added to induce crystallization. Results summarized in Table 23 showed only Form A was obtained.

TABLE 23

Summary of slurry conversion experiments at 50° C.

| Solvent (v/v) | Solid Form |
|---|---|
| MTBE | Form A* |
| Toluene | Form A* |
| $H_2O$ | Form A |

*Solids were obtained after anti-solvent addition of n-heptane.

Example 19: Liquid Vapor Diffusion Experiments

Liquid Vapor Diffusion experiments were performed. Four liquid vapor diffusion experiments were conducted.

Approximately 15 mg of Form A was dissolved in 0.5 mL of solvent to obtain a clear solution in a 3-mL vial. This solution was then placed into a 20-mL vial with 4 mL of anti-solvent. The 20-mL vial was sealed with a cap and kept at RT for organic vapor to interact with the solution. The precipitates were isolated for XRPD analysis. The results summarized in Table 24 showed that Form A and Form B were obtained.

TABLE 24

Summary of liquid vapor diffusion experiments.

| Solvent | Anti-solvent | Solid Form |
|---|---|---|
| THF | H$_2$O | Form A |
| EtOH | | Forin A |
| EtOAc | n-heptane | Form B |
| CHCl$_3$ | | Form A |

Example 20: Interconversion Study

An interconversion study of crystal forms was performed. To understand the thermodynamic stability relationship between Form A and B, competitive slurry experiments were performed at RT and 50° C. in water and toluene. Prior to the study, Form A was used to saturate the corresponding solvent before it was filtered to obtain a near-saturated solution. Equal amounts of Form A and B samples were weighed and then mixed with the prepared near-saturated solution to form a new suspension, which was stirred magnetically (~1000 rpm) at RT and 50° C. As summarized in Table 25, Form A was obtained after slurry at RT and 50° C. for 1~3 weeks, indicating that Form A was thermodynamically more stable than Form B from RT to 50° C.

TABLE 25

Thermodynamic stability study.

| Starting Form | Solvent (v/v) | Temperature | Final Form |
|---|---|---|---|
| Form A + B | H$_2$O/PhMe | RT | Form A |
| Form A + B | H$_2$O/PhMe | 50° C. | Form A |

Example 21: Competitive Slurry Study

A competitive slurry study of all known forms A to E was performed in water at room temperature to understand the thermodynamic stability relationship among these forms. Form A was used to saturate the water before it was filtered to obtain a near-saturated solution. Equal amounts of each form (A to E) were weighed and then mixed with the prepared near-saturated solution to form a new suspension, which was stirred magnetically (~1000 rpm) at room temperature for 7 days. Solids were isolated and analyzed by XRPD and Form A was obtained indicating that Form A was thermodynamically the most stable form at RT.

Example 22: Vapor Induced Crystallization Experiments

A total of 9 different experiments were conducted. About 100 mg of Form B was placed in a 4 mL glass vial which was then placed into a 20-mL vial with 4 mL of anti-solvent in it. The 20-mL vial was sealed with a cap and kept at RT for organic vapor to interact with the solid. After 7 to 10 days, wet solids were isolated and analyzed by XRPD. The results summarized in Table 26 showed that Form A and Form B were obtained.

TABLE 26

Summary of vapor induced crystallization experiments

| Condition | Result |
|---|---|
| Ethanol | Form A |
| DMSO | Form A |
| Isopropyl Acetate | Form A |
| Methyl Acetate | Form B |
| THF | Clear film after evaporation |
| CH$_2$Cl$_2$ | Form B |
| Cyclohexanone | Form A |
| Dimethyl Formamide | Form A |
| N-butyl Acetate | Form A |

Characterization Methodology

Samples generated as described in the solid form screen were typically analyzed by X-Ray Powder Diffraction (XRPD). XRPD was conducted on a PANalytical Empyrean and X'Pert3 X-ray powder diffractometer using Cu Kα radiation at 1.54 Å. In general, positions of XRPD peaks are expected to individually vary on a measurement-by-measurement basis by about ±0.2° 2θ. In general, as understood in the art, two XRPD patterns match one another if the characteristic peaks of the first pattern are located at approximately the same positions as the characteristic peaks of the second pattern. As understood in the art, determining whether two XRPD patterns match or whether individual peaks in two XRPD patterns match may require consideration of individual variables and parameters such as, but not limited to, preferred orientation, phase impurities, degree of crystallinity, particle size, variation in diffractometer instrument setup, variation in XRPD data collection parameters, and/or variation in XRPD data processing, among others. The determination of whether two patterns match may be performed by eye and/or by computer analysis. An example of an XRPD pattern collected and analyzed using these methods and parameters is provided herein, e.g., as FIG. 1.

PANalytical Empyrean
Scan Mode: Continuous
Detector: D/teX Ultra
Divergence slit: Automatic
Start Angle: 3 deg.
Stop Angle: 40 deg.
Step Width: 0.0200 deg.
Scan time (s): 5.00 deg./min
Incident Slit: ½ deg.
Receiving Slit #1: 8.000 mm
Receiving Slit #2: 13.000 mm
Wavelength: Kα1: 1.540598 Å; Kα2: 1.5444426 Å; intensity ratio Kα2/Kα1: 0.50; 40 kV, 44 mA.
X'Pert3
Scan Mode: Continuous
Divergence slit: ⅛°
Start Angle: 3 deg
Stop Angle: 40 deg.
Step Size: 0.0263 deg.
Scan step time (s): 46.665
Test time: about 5 minutes
Wavelength: Kα1: 1.540598 Å; Kα2: 1.5444426 Å; intensity ratio Kα2/Kα1: 0.50

Differential Scanning Calorimetry (DSC) analyses were performed on a TA Instruments Q200/Q2000. About 5 mg of sample was placed into a tared DSC crimped/open aluminum pan and the weight of the sample was accurately recorded. The heating rate was 10° C./min, using nitrogen as the purge gas. An example of a DSC thermogram collected and analyzed using these methods and parameters is provided herein, e.g., as FIG. 2.

Thermal Gravimetric Analyses (TGA) were performed on a TA Instruments Q500/Q5000. About 10 mg of sample was placed on an open aluminum pan, accurately weighed and loaded into the TGA furnace. The heating rate was 10° C./min, using nitrogen as the purge gas. An example of a TGA thermogram collected and analyzed using these methods and parameters is provided herein, e.g., as FIG. 2.

Dynamic vapor sorption (DVS) was performed on a Surface Measurement Systems DVS Intrinsic. The relative humidity at 25° C. were calibrated against deliquescence point of LiCl, $Mg(NO_3)_2$, and KCl. Sample sizes were between 10-20 mg. Gas and flow rate was nitrogen, 200 mL/min; dm/dt: 0.002%/min.

HPLC was performed with Agilent 1100/1260. The analysis for Form A was determined with a Phenomenex Gemini C18, 150×4.6 mm, 3 μm (column). The mobile phase was 0.1% formic acid in water; flow rate of 1.0 mL/min; column temperature of 40° C.; and UV detector at 270 nm. The analysis for Form B was determined with a Kinetex 5 μm EVO C18, 150×4.6 mm, 5 μm (column). The mobile phase was 0.1% formic acid in acetonitrile; flow rate of 1.0 mL/min; column temperature of 40° C.; and UV detector at 210 nm.

Proton NMR was collected on Bruker 400 NMR Spectrometer using $DMSO_{d6}$.

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the disclosure and are encompassed by the appended claims.

Citation or identification of any reference in this application is not an admission that such reference is available as prior art. The full scope of the disclosure is better understood with reference to the appended claims.

The invention claimed is:

1. A method of treating pain compromising administering to a subject a composition comprising a crystalline form of (R)-5-carbamoylpyridin-3-yl-2-methyl-4-(3-(trifluoromethoxy)benzyl)piperazine-1-carboxylate, wherein:
   the crystalline form is Form A of (R)-5-carbamoylpyridin-3-yl-2-methyl-4-(3-(trifluoromethoxy)benzyl)piperazine-1-carboxylate, having an X-ray powder diffraction pattern comprising peaks at 18.1, 20.1, and 22.3 degrees 2θ±0.2 degrees 2θ;
   the crystalline form is Form B of (R)-5-carbamoylpyridin-3-yl-2-methyl-4-(3-(trifluoromethoxy)benzyl)piperazine-1-carboxylate, having an X-ray powder diffraction pattern comprising peaks at 16.2, 18.2, and 19.2 degrees 2θ±0.2 degrees 2θ;
   the crystalline form is Form C of (R)-5-carbamoylpyridin-3-yl-2-methyl-4-(3-(trifluoromethoxy)benzyl)piperazine-1-carboxylate, having an X-ray powder diffraction pattern comprising peaks at 18.0, 20.0, and 21.0 degrees 2θ±0.2 degrees 2θ;
   the crystalline form is Form D of (R)-5-carbamoylpyridin-3-yl-2-methyl-4-(3-(trifluoromethoxy)benzyl)piperazine-1-carboxylate, having an X-ray powder diffraction pattern comprising peaks at 13.4, 21.0, and 23.8 degrees 2θ±0.2 degrees 2θ; or
   the crystalline form is Form E of (R)-5-carbamoylpyridin-3-yl-2-methyl-4-(3-(trifluoromethoxy)benzyl)piperazine-1-carboxylate, having an X-ray powder diffraction pattern comprising peaks at 17.8, 21.3, and 22.8 degrees 2θ±0.2 degrees 2θ.

2. The method of claim 1, wherein the pain is neuropathic pain.

3. The method of claim 1 or claim 2, wherein the crystalline form is Form A of (R)-5-carbamoylpyridin-3-yl-2-methyl-4-(3-(trifluoromethoxy)benzyl)piperazine-1-carboxylate, having an X-ray powder diffraction pattern comprising peaks at 18.1, 20.1, and 22.3 degrees 2θ±0.2 degrees 2θ.

4. The method of claim 3, wherein the X-ray powder diffraction pattern further comprises peaks at 9.9, 19.9, and 24.7 degrees 2θ±0.2 degrees 2θ.

5. The method of claim 1 or claim 2, wherein the crystalline form is Form B of (R)-5-carbamoylpyridin-3-yl-2-methyl-4-(3-(trifluoromethoxy)benzyl)piperazine-1-carboxylate, having an X-ray powder diffraction pattern comprising peaks at 16.2, 18.2, and 19.2 degrees 2θ±0.2 degrees 2θ.

6. The method of claim 5, wherein the X-ray powder diffraction pattern further comprises peaks at 15.1, 18.7, and 20.1 degrees 2θ±0.2 degrees 2θ.

7. The method of claim 1 or claim 2, wherein the crystalline form is Form C of (R)-5-carbamoylpyridin-3-yl-2-methyl-4-(3-(trifluoromethoxy)benzyl)piperazine-1-carboxylate, having an X-ray powder diffraction pattern comprising peaks at 18.0, 20.0, and 21.0 degrees 2θ±0.2 degrees 2θ.

8. The method of claim 7, wherein the X-ray powder diffraction pattern further comprises peaks at 12.3, 16.8, and 25.5 degrees 2θ±0.2 degrees 2θ.

9. The method of claim 1 or claim 2, wherein the crystalline form is Form D of (R)-5-carbamoylpyridin-3-yl-2-methyl-4-(3-(trifluoromethoxy)benzyl)piperazine-1-carboxylate, having an X-ray powder diffraction pattern comprising peaks at 13.4, 21.0, and 23.8 degrees 2θ±0.2 degrees 2θ.

10. The method of claim 9, wherein the X-ray powder diffraction pattern further comprises peaks at 18.3, 26.7, and 29.5 degrees 2θ±0.2 degrees 2θ.

11. The method of claim 1 or claim 2, wherein the crystalline form is Form E of (R)-5-carbamoylpyridin-3-yl-2-methyl-4-(3-(trifluoromethoxy)benzyl)piperazine-1-carboxylate, having an X-ray powder diffraction pattern comprising peaks at 17.8, 21.3, and 22.8 degrees 2θ±0.2 degrees 2θ.

12. The method of claim 11, wherein the X-ray powder diffraction pattern further comprises peaks at 15.8, 18.4, and 21.9 degrees 2θ±0.2 degrees 2θ.

* * * * *